US007056696B1

(12) United States Patent
Iba et al.

(10) Patent No.: US 7,056,696 B1
(45) Date of Patent: *Jun. 6, 2006

(54) EXPRESSION VECTOR CONTAINING A DRUG-RESISTANCE GENE HAVING A DESTABILIZING SEQUENCE AS SELECTION MARKER

(75) Inventors: Hideo Iba, Kanagawa (JP); Tohru Arai, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/800,520

(22) Filed: Mar. 8, 2001

Related U.S. Application Data

(63) Continuation of application No. 09/214,465, filed as application No. PCT/JP97/04592 on Dec. 12, 1997, now Pat. No. 6,743,620.

(30) Foreign Application Priority Data

Dec. 16, 1996 (JP) .................................. 8-335433
Jun. 17, 1997 (JP) .................................. 9-159538

(51) Int. Cl.
C12N 15/867 (2006.01)
C12N 5/10 (2006.01)
C12N 15/63 (2006.01)
C12P 19/34 (2006.01)
A01N 43/04 (2006.01)

(52) U.S. Cl. .................. 435/69.1; 435/320.1; 435/325; 435/70.1; 435/91.1; 435/455; 435/456

(58) Field of Classification Search ................ 536/23.1, 536/23.4, 24.1; 530/350; 435/69.7, 69.1, 435/183
See application file for complete search history.

(56) References Cited

U.S. PATENT DOCUMENTS

| 5,194,376 A | 3/1993 | Kang |
| 5,304,640 A | 4/1994 | Lasky et al. |
| 5,629,159 A | 5/1997 | Anderson |
| 5,965,393 A | 10/1999 | Hasnain et al. |
| 5,972,596 A * | 10/1999 | Pavlakis et al. |
| 6,087,129 A * | 7/2000 | Newgard et al. .......... 435/69.4 |
| 6,214,578 B1 | 4/2001 | Ueki et al. |
| 6,218,187 B1 | 4/2001 | Finer et al. |
| 6,506,604 B1 | 1/2003 | Finer et al. |
| 6,635,472 B1 | 10/2003 | Lauermann |
| 6,743,620 B1 | 6/2004 | Iba et al. |
| 6,746,860 B1 | 6/2004 | Tokusumi et al. |
| 6,902,929 B1 | 6/2005 | Cichutek et al. |

FOREIGN PATENT DOCUMENTS

| WO | WO 96/14395 | 5/1996 |
| WO | WO 96/40955 | 12/1996 |

OTHER PUBLICATIONS

DePonti-Zilli et al. A 40-base-pair sequence i the 3'end of the B-actin gene regulates B-actin mRNA transcription during myogenesis vol. 85 pp. 1389-1393 1988.*
Gritz, et al. Gene, vol. 25, pp. 179-188, 1983.*
de la Luna, et al. Gene, vol. 62, pp. 121-126, 1988.*
Treisman, Richard. Cell, vol. 42, pp. 889-902, 1985.*
The 1995 Pharmacia Biotech Catalog, pp. 128-129.*
Schuler, et al. Cell. vol. 55, pp. 1115-1122, Dec. 1998.*
Stephen Hardy et al, Journal of Virology (1997) vol. 71, No. 3, p. 1842-1849, "Construction of Adenovirus Vectors through Cre-lox Recombination".
Corinne Fernex et al, Journal of Virology (1997) vol. 71, No. 10, p. 7533-7540, "Cre/loxP-Mediated Excision of a Neomycin Resistance Expression Unit from an Integrated Retroviral Vector Increases Long Terminal Repeat-Driven Transcription in Human Hematopoietic Cells".
Andreas P. Russ et al, Journal of Viroloty (1996) vol. 70, No. 8, p. 4927-4932, "Self-Deleting Retrovirus Vectors for Gene Therapy".
Y. Wang et al, Proc. Natl. Acad. Sci. USA (1996) vol. 93, p. 3932-3936, "Targeted DNA recombination in vivo using an adenovirus carrying the crerecombinase gene".
Proc. Natl. Acad. Sci. USA (1996) vol. 93, p. 13565-13570, "A helper-dependent adenovirus vector system: Removal of helper virus by Cre-mediated excision of the viral packaging signal", Robin J. Parks et al.
Miller, J. Amer Society of Hematology vol. 76, No. 2 1990 pp. 271-278 Blood.
Marshall, Science, vol. 269, pp. 1050-1055 Aug. 1995 Gene Therapy's Growing Pains.
Vile, Gene Therapy Dec. 30, 1995 Combination Gene Therapies for the Immunotherapy of Cancer.
Zavada, Arch of Virology 50, Jan. 15, 1976 Viral Pseudotypes and Phenotypic Mixing.
Emi et al J. of Virology, vol. 65, No. 3 Mar. 1991 pp. 1202-1207 Psuedotype Formation of Murine Leukemia etc.
Yee et al Proc. Natl Acad Sci USA vol. 91, pp. 9564-9568 Sep. 1994 Genetics A general method for the generation of high-titer, pantropic retroviral vectors: Highly efficient infection of primary hepatocytes.

(Continued)

Primary Examiner—David Guzo
Assistant Examiner—Laura McGillem
(74) Attorney, Agent, or Firm—Nixon & Vanderhye P.C.

(57) ABSTRACT

The present invention provides a process for preparing a retrovirus to be expressed at a high titer by specifically transferring a desired foreign gene into target cells. A pseudotyped retrovirus vector having a high titer can be prepared by transferring a DNA construction wherein a promoter, a loxP sequence, a VSV-G gene and a polyA addition signal are arranged in this order is transferred into cells carrying the retrovirus gag and pol gene expression systems, and then transferring a retrovirus vector containing the desired foreign gene thereinto, followed by the treatment with a recombinase.

18 Claims, 11 Drawing Sheets

OTHER PUBLICATIONS

Yang et al Human Gene Therapy vol. 6, pp. 1203-1213 1995 Inducible, High Level Production of Infectious Murine Leukemia Retroviral Vector Particles Pseydotyped etc.
Chen et al Proc. Natl. Acad. Sci. USA vol. 93, pp. 10057-10062 Sep. 1996 Generation for packaging cell lines etc.
Ory et al Proc. Natl. Acad. Sci. USA vol. 93, pp. 11400-11406 Oct. 1996 A Stable human derived packaging cell etc.
Pear et al Proc. Natl. Acad. Sci. USA vol. 90, pp. 8392-8396 Sep. 1993 Production of High-titer helper-free retroviruses by transient infection.
Chen, C.A., et al. Mol. Cell. Biol. 14:8471-8482 (1994).
Shyu, et al., Genes Dev. 3:60-72 (1989).
Arai et al. "A new system for stringent, high-titer vesicular stomatitis virus G protein-pseudotyped retrovirus vector induction by introduction of Cre recombinase into stable prepackaging cell lines" XP-000857996 J. Virol. 72:1115-1121 (1998).
Kanegae et al. "Efficient gene activation in mammalian cells by using recombinant adenovirus expressing site-specific Cre recombinase" XP-002006337 Nucl. Acids Res. 23:3816-3821 (1995).
Kanegae et al. "Efficient gene activation system on mammalian cell chromosomes using recombinant adenovirus producing Cre recombinase" Gene 181:207-212 (1996).
Ui et al. "Retrovirus vectors designed for efficient transduction of cytotoxic or cytostatic genes" XP-009007601 Gene Therapy 6:1670-1678 (1999).
Wang et al. "High frequency recombination between loxP sites in human chromosomes mediated by an adenovirus vector expressing Cre recombinase" XP-000617918 Somatic Cell and Molecular Genetics 21:429-441 (1995).
Lagnado et al. "AUUUA is not sufficient to promote poly(A) shortening and degradation of an mRNA: The functional sequence within AU-rich elements may be UUAUUUA(U/A)(U/A)" Mol. Cell. Biol. 14:7894-7995 (1994).
Agapov et al. "Noncytopathic Sindbis virus RNA vectors for heterologous gene expression" Proc. Natl. Acad. Sci. USA 95:12989-12994 (1998).
Bergemann et al. "Excision of specific DNA-sequences from integrated retroviral vectors via site-specific recombination" Nucl. Acids Res. 23:4451-4456 (1995).
Bukreyev et al. "Recovery of infectious respiratory syncytial virus expressing an additional, foreign gene" J. Virol. 70:6634-6641 (1996).
Jarvis et al. "Immediate early baculovirus vectors for foreign gene expression in transformed or infected insect cells" inNovations 5:1-5 (1996).
Johanning et al. "A sindbis virus mRNA polynucleotide vector achieves prolonged and high level heterologous gene expression in vivo" Nucl. Acids Res. 23:1495-1501 (1995).
Ou-Lee et al. "Expression of a foreign gene linked to either a plant-virus or a *Drosophila* promoter, after electroporation of protoplasts of rice, wheat, and sorghum" Proc. Natl. Acad. Sci. USA 83:6815-6819 (1986).
Park et al. "Rescue of a foreign gene by Sendai virus" Proc. Natl. Acad. Sci. USA 88:5537-5541 (1991).
Vento et al. "Fact sheet describing recombinant DNA and elements utilizing recombinant DNA such as plasmids and viral vectors, and the application of recombinant DNA techniques in molecular biology" Office of Environment Health and Safety, University of New Hampshire (2002).
*The American Heritage Dictionary of the English Language, Fourth Edition*, Houghton Mifflin Co., entry for "heterologous" (2000).

* cited by examiner pCALNLG pCALNdLG mRNA destabilizing signal pBabe related plasmid pBabe loxpuro pBabe loxpuroΔpA  pBabeloxpuro without pA SD-: mutation at splice donor site
ATG-: mutation at *gag* first Met
SV40: SV40 early promoter
*puro^r*: puromycin resistant gene
pA: SV40 polyA signal a "fresh" was thawed freshly prior to use.
"old" was cultured for 2 months.

b

"fresh" was thawed freshly prior to use.
"old" was cultured for 2 months.

a b days after Cre recombinase introduction days after Cre recombinase introduction days after Cre recombinase introduction

EXPRESSION VECTOR CONTAINING A DRUG-RESISTANCE GENE HAVING A DESTABILIZING SEQUENCE AS SELECTION MARKER This is a continuation of application Ser. No. 09/214,465, filed Jan. 5, 1999, now U.S. Pat. No. 6,743,620; which is a national-stage application filed under 35 U.S.C. 371 of Int'l Appln. No. PCT/JP97/04592, filed Dec. 12, 1997, the entire content of which is hereby incorporated by reference in this application.

BACKGROUND OF THE INVENTION

1. Technical Field

The present invention relates to a process for preparing a retrovirus vector having a high titer and employed in gene therapy.

2. Prior Art

Owing to the remarkable progress in genetic engineering in recent years, there have been identified genes causative of a number of genetic diseases and thus the pathological mechanisms of these diseases have been clarified at the molecular level. Under these circumstances, studies on gene therapy have been made to transfer genes seemingly capable of ameliorating diseases into cells and some of these treatments have been already put into practical use. Also, attempts have been made to apply the gene therapy to the treatment of cancer, AIDS, etc. In gene therapy, there are known several methods for transferring foreign genes. Among all, the most frequently employed method at the present stage is the one with the use of retrovirus vectors (Miller, A. D., Blood, 76, 271–278, 1990). Use of these vectors has the following advantages. Since the transferred gene can be surely integrated into chromosomes, it can be expressed stably over a long period of time. In addition, this method is a highly safe one with little fear of cytotoxicity. On the other hand, this method suffers from some problems such that no gene can be transferred into cells in a number of cases because of the absence of any receptor for virus envelope proteins in the target cells, that large-sized DNAs cannot be inserted thereby, and that the gene transfer thereby is available exclusively into cells which are capable of dividing. Although gene therapy with the use of retroviruses has been frequently employed, no sufficient therapeutic effect can be achieved thereby hitherto because of the above problems (Marshall, E., Science, 269, 1050–1055, 1995).

To effect the gene therapy, anyway, it is required to satisfy at least the following three conditions: 1) to efficiently transfer a desired gene into the target cells; 2) to ensure the continuous expression of the transferred gene; and 3) to be safe for the environment including the patient.

The conventional process for preparing a retrovirus vector comprises transferring a retrovirus genome containing a desired foreign gene into cells called packaging cells wherein retrovirus gag, pol and env have been expressed stably to thereby give a retrovirus containing the foreign gene in its vector DNA. However, it is difficult to prepare vectors with such high qualities as usable for clinical purposes by this process. Thus, a number of studies have been made to prevent the occurrence of a replication competent retrovirus (RCR), to produce a retrovirus having a high titer, and to elevate the titer of a retrovirus vector by improving the vector genome structure or examining the conditions for condensation or gene transfer (Vile, R. G., Gene Therapy, Churchill Livingstone, 12–30, 1995). In spite of these efforts, no technique has been established so far for a vector having a broad infection range and a high titer in a large scale stably, which is one of serious obstacles to the gene therapy.

Meanwhile, studies have been energetically made for a long time by using vesicular stomatitis virus (VSV) as a model of pseudotyped viruses as the joint between retroviruses and other viruses (Zavada, J., Arch. Virol., 50, 1, 1976). The term "pseudotype" means a phenomenon wherein a virus genome germinates while being surrounded by the coat protein of another virus. VSV is a virus having a negative single-stranded RNA genome and belonging to the family Rhabdovirus. It is considered that the receptors on the cell surface of the coat protein (G protein) thereof include anionic lipids such as phosphatidylserine. Thus, it is known that VSV has an extremely broad host range. It is therefore assumed that by preparing a pseudotyped retrovirus having this VSV-G gene product in the coat, genes can be efficiently transferred into cells which can be transduced at only a low or even no infective efficiency with retroviruses having the inherent envelope protein. In fact, Emi et al. (Emi, N., et al., J. Virol., 65, 1202–1207, 1991) and Yee et al. (Yee, J. K., et al., Proc. Natl. Acad. Sci. USA, 91, 9564–9568, 1994) reported a process for preparing a retrovirus vector having a VSV-G gene product as its envelope and pointed out that this pseudotyped virus enabled efficient gene transfer into cells which could have been transduced only at a low infective efficiency with a retrovirus having the inherent envelope protein.

To clinically apply such a VSV-G pseudotyped virus vector, it is necessary to establish a method for acquiring a virus with a high titer at a high reproducibility. However, it is difficult to produce the VSV-G gene product at a high level and at a high reproducibility in packaging cells, since the VSV-G gene product per se has a cytotoxicity. This is a serious problem in the development of pseudotyped vectors which are expected to be widely applicable. Recently, it was reported that VSV-G pseudotyped virus vector-producing cells can be prepared by regulating the expression of the VSV-G gene product with the use of tetracycline (Yang, Y., et al. Hum. Gene. Ther., 6, 1203–1213, 1995; Chen, S. T., et al., Prc. Natl. Acad. Sci. USA, 93, 10057–10062, 1996; and Ory, D. S., et al., Proc. Natl. Acad. Sci. USA, 93, 11400–11406, 1996). However, there still remain some problems in these reports such that the regulation of the expression of the VSV-G gene product was not completely regulated by tetracycline and, therefore, the producing cells might be still re-infected with about $10^2$ to $10^4$ i.u./ml of the VSV-G pseudotyped virus vector thus produced; and that the stability of the packaging cells over a long period of time was still unreliable, since they were made of the co-transfection of a DNA with the VSV-G expression and another DNA with the drug-resistance gene expression.

It is also known that, when a foreign gene to be transferred into target cells with the use of a retrovirus strongly affects the cells, the virus carrying this foreign gene in its virus vector DNA cannot be recovered stably, since the foreign gene product affects in the virus-producing cells (i.e., the packaging cells containing and expressing the vector DNA) per se (Pear, W. S. et al., Proc. Natl. Acad. Sci. USA, 90, 8392–8396, 1993).

In the present description, the term "pseudotyped virus vector" refers to a retrovirus vector having a VSV-G gene product in its envelope, while the term "retrovirus vector" refers to both a retrovirus vector having the inherent envelope protein and a "pseudotyped virus vector".

The term "prepackaging cells" refers to cells in which gag and pol of a retrovirus can be expressed and env thereof cannot be expressed in usual before recombinase was introduced to cells. The term "prepackaging cells containing a vector DNA" refers to the prepackaging cells as defined above into which a vector DNA has been transferred. Further, the term "packaging cells containing a vector DNA" refers to cells capable of producing a virus when a recombinase is transferred thereinto.

Moreover, the term "drug resistance gene" as used herein refers to all of low-efficient drug resistance genes, short-lived transcript drug resistance genes having a base sequence of a short-lived mRNA of a drug resistance gene and conventional drug resistance genes.

DISCLOSURE OF INVENTION

Under these circumstances, an object of the present invention is to establish a process whereby a retrovirus vector for specifically transferring foreign genes including those affecting cells into target cells over a broad range and expressing the genes therein can be stably produced at a high titer by strictly regulating, compared with the conventional processes, cytotoxic virus structural proteins and vector DNA with a cytotoxic or cell-affecting protein; to establish a process for elevating the recovery yield of a retrovirus vector by inhibiting the reinfection of producing cells with a pseudotyped retrovirus vector; and to efficiently screen high-expression cell clones by using a low-efficient drug resistance gene or a short-lived transcript drug resistance gene in the transcription of two genes by a recombinase with the use of the same promoter.

To solve the above problems, the present inventors have conducted intensive studies.

A DNA wherein an loxP sequence, a drug resistance gene, a polyA addition signal, an loxP sequence, a VSV-G gene and a polyA addition signal are arranged in this order in the downstream of a potent promoter is transferred into cells having gag and p01 genes of a retrovirus transferred thereinto. Then the resultant cells are screened with the use of the drug to prepare prepackaging cells. The prepackaging cells thus prepared are transduced with a retrovirus vector containing a desired gene inserted in its vector DNA to thereby transfer the gene into the prepackaging cells. At the same time, a recombinase is introduced to the cell. Thus, the VSV-G gene product can be expressed at a high level within a short period of time with the use of the same potent promoter as the one employed for expressing the drug resistance gene. As a result, a pseudotyped virus vector having a high titer can be successfully prepared in a large amount prior to the appearance of the cytotoxicity of both the VSV-G gene product and foreign gene product in vector DNA. The present invention has been thus completed.

The present inventors have also found out that the producing cells are reinfected with the pseudotyped retrovirus vector and the reinfection can be inhibited by adding a negatively charged, high-molecular weight substance to the liquid culture medium, thus enhancing the recovery yield.

They have also utilized the phenomenon that, in the preparation of the above-mentioned prepackaging cells, cells requiring the expression of a stronger resistance marker can be efficiently screened by using as a drug resistance marker gene one the function of which has been deteriorated by substitution, insertion or deletion in the base sequence in the coding region, one the translation efficiency of which has been lowered by substitution, insertion or deletion in the base sequence in the untranslated region (i.e., a low-efficient drug resistance gene), or one the stability of the mRNA produced by which has been lowered (i.e., a short-lived transcript drug resistance gene). In the present invention, use is made of these short-lived transcript drug resistance genes thus devised. Furthermore, it has become possible to establish the enhanced expression of the VSV-G gene product by transferring into the cells a retrovirus vector having the desired gene or its DNA inserted thereinto and treating with a recombinase. Thus, the present inventors have succeeded in the production of a large amount of a pseudotyped vector having a high titer.

DETAILED DESCRIPTION OF THE INVENTION

The present invention relates to processes for preparing retrovirus vectors for gene therapy which comprise transferring a DNA construction (hereinafter referred to as a DNA construction (A)) for regulating the expression of a virus structural protein by using a recombinase and its recognition sequence and another DNA construction (hereinafter referred to as a DNA construction (B)) for regulating the expression of a foreign gene encoded in a vector DNA, by using a recombinase and its recognition sequence into retrovirus gag-pol-producing cells followed by the transfer of a DNA with the recombinase expression thereinto. More particularly, it relates to: 1) a process for preparing a retrovirus vector for gene therapy which comprises transferring a DNA construction (A) wherein a promoter, a recombinase recognition sequence, a drug resistance gene, a polyA addition signal, a recombinase recognition sequence, a virus structural protein gene and a polyA addition signal are arranged in this order and another DNA construction (B) wherein the LTR of a retrovirus genome and a packaging signal are followed by a recombinase recognition sequence, a drug resistance gene, a polyA addition signal, a recombinase recognition sequence, a foreign gene and LTR arranged in this order into retrovirus gag-pol-producing cells followed by the transfer of a DNA with the recombinase expression thereinto; 2) a process for preparing a retrovirus vector for gene therapy which comprises transferring into retrovirus gag-pol-env-producing cells a DNA construction (B) wherein the LTR of a retrovirus genome and a packaging signal are followed by a recombinase recognition sequence, a drug resistance gene, a polyA addition signal, a recombinase recognition sequence, a foreign gene and LTR arranged in this order followed by the transfer of a DNA with the recombinase expression thereinto; 3) a process for preparing a retrovirus vector for gene therapy which comprises transferring a DNA construction (A) wherein a promoter, a recombinase recognition sequence, a drug resistance gene, a polyA addition signal, a recombinase recognition sequence, a virus structural protein gene and a polyA addition signal are arranged in this order and a retrovirus vector DNA encoding a foreign gene into retrovirus gag-pol-producing cells followed by the transfer of a DNA with the recombinase expression thereinto; 4) a DNA construction (A) wherein a promoter, a recombinase recognition sequence, a drug resistance gene, a polyA addition signal, a recombinase recognition sequence, a virus structural protein gene and a polyA addition signal are arranged in this order; 5) a DNA construction (B) wherein the LTR of a retrovirus genome and a packaging signal are followed by a recombinase recognition sequence, a drug resistance gene, a polyA addition signal, a recombinase recognition sequence, a foreign gene and LTR arranged in this order; 6) a DNA construction (A) wherein the promoter is CAG; 7) a DNA construction (A) or a DNA construction (B) wherein the recombinase and its recognition sequence are Cre recombinase and loxP sequence respectively; 8) a DNA construction (A) or a DNA construction (B) wherein the drug resistance gene is a neomycin-resistance gene, a puromycin-resistance gene or a hygromycin-resistance gene; 9) a DNA construction (A) or a DNA construction (B) wherein the drug resistance gene is a low-efficient drug resistance gene or a short-lived transcript drug resistance gene having a short-lived mRNA base sequence; 10) a DNA construction (A) or a DNA construction (B) wherein the low-efficient drug resistance gene or the short-lived transcript drug resistance gene is one originating in a neomycin resistance gene, a puromycin resistance gene or a hygromycin resistance gene; 11) a short-lived transcript drug resistance gene characterized by having a short-lived mRNA base sequence of a neomycin resistance gene, a puromycin resistance gene or a hygromycin resistance gene; 12) a short-lived transcript drug resistance gene wherein the mRNA has been made short-lived with an mRNA-unstabilizing signal originating in c-fos; 13) a DNA construction (A) or a DNA construction (B) wherein the polyA addition signal is one originating in SV40 or β-globin; 14) a DNA construction (A) wherein the virus structural protein gene is a DNA encoding vesicular stomatitis virus (VSV) G protein (VSV-G); 15) the DNA construction (B) as set forth in Claim 2, wherein the retrovirus genome is one originating in Moloney murine leukemia virus (MoMLV); 16) a DNA construction (B) wherein the retrovirus genome is one originating in a lentivirus; 17) a DNA construction (B) wherein the foreign gene is a gene aiming at cell transfer for gene therapy; 18) a DNA construction (B) wherein the foreign gene is a gene of a cytotoxic protein; 19) a DNA construction (A) wherein a CAG promoter, an loxP sequence, a drug resistance gene, a polyA addition signal, an loxP sequence, a VSV-G gene and a polyA addition signal are arranged in this order; 20) a DNA construction (B) wherein the LTR of a retrovirus genome and a packaging signal are followed by an loxP sequence, a drug resistance gene, a polyA addition signal, an loxP sequence, a foreign gene and LTR arranged in this order; 21) a prepackaging cell for producing a retrovirus vector wherein a DNA construction (A) has been transferred into a retrovirus gag-pol-producing cell; 22) a virus vector DNA-containing prepackaging cell for producing a retrovirus vector wherein a DNA construction (B) has been transferred into a retrovirus gag-pol-env-producing cell; 23) a virus vector DNA-containing prepackaging cell for producing a retrovirus vector wherein a DNA construction (A) and a DNA construction (B) have been transferred into a retrovirus gag-pol-producing cell; 24) a virus vector DNA-containing prepackaging cell for producing a retrovirus vector wherein a DNA construction (A) and a virus vector DNA encoding a foreign gene have been transferred into a retrovirus gag-pol-producing cell; 25) a prepackaging cell for producing a retrovirus vector wherein the retrovirus is murine leukemia virus (MLV); 26) a process for preparing a pseudotyped retrovirus wherein a negatively charged, high-molecular weight substance is contained in the liquid culture medium; and 27) a process for producing a pseudotyped retrovirus wherein the negatively charged, high-molecular weight substance is one selected from among heparin, heparan sulfate and chondroitin sulfate.

BRIEF DESCRIPTION OF DRAWINGS

FIG. 1 summarizes the invention relating to a retrovirus vector for gene therapy prepared by the process according to the present invention.

Figure 1:
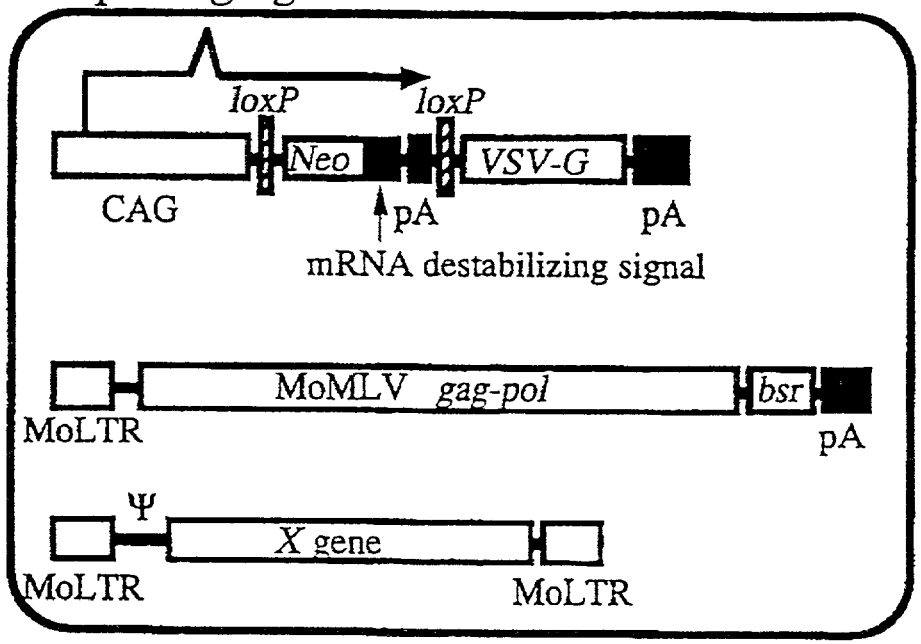
FIG. 1 schematically illustrates a system for producing a pseudotyped retrovirus by prepackaging cells.
Figure 1:
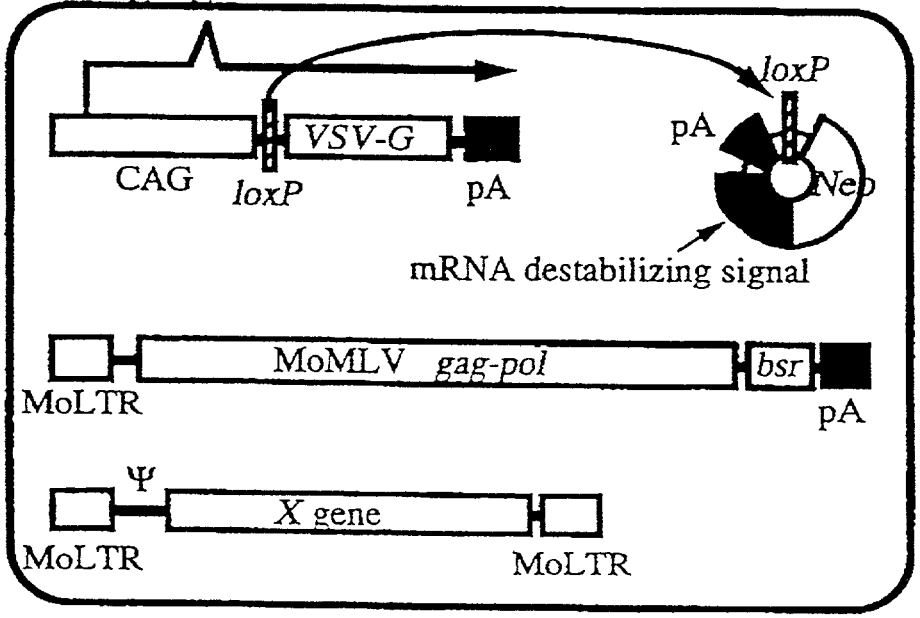

A recombinase is an enzyme participating in a DNA site-specific recombination which catalyzes by itself a series of reactions required in the site-specific recombination, i.e., recognition of a specific base sequence, cleaving of the same, and binding. More particularly, use can be made therefor of a recombinase encoded by an FLP gene originating in a yeast 2μ plasmid, a recombinase originating in pSR1 plasmid of *Schizosaccharomyces louii*, a Cre recombinase encoded by a P1 phage of *Escherichia coli*, etc. each combined with the recognition sequence corresponding thereto. The Cre recombinase may be proposed as a preferable recombinase. The Cre recombinase is an enzyme which specifically recognizes an loxP sequence of 34 base pairs (Fukushige, S., et al., Proc. Natl. Acad. Sci. USA, 89, 6323–6236, 1992). When a recombinant vector having two copies of this loxP sequence in the same direction is constructed and treated with the Cre recombinase, there arises a recombination between these two loxP sequences and the region located between these sequences is cut off therefrom as a cyclic molecule. This process is called the Cre/loxP system.

A DNA construction (A) which regulates the expression of a virus structural protein gene by using a recombinase and its recognition sequence carries a promoter, the recombinase recognition sequence, a drug resistance gene, a polyA addition signal, the recombinase recognition sequence, the virus structural protein gene and a polyA addition signal arranged in this order. On the other hand, a DNA construction (B) which regulates the expression of a foreign gene by using a recombinase and its recognition sequence carries the LTR of a retrovirus genome and a packaging signal followed by the recombinase recognition sequence, a drug resistance gene, a polyA addition signal, the recombinase recognition sequence, the foreign gene and LTR arranged in this order. In these cases, the drug resistance gene alone is transcribed in the promoter (or LTR in the DNA construction (B)). When such a construction is transferred into cells, therefore, the cells can be selected by using the drug resistance. When the cells thus screened are treated by introducing of the Cre recombinase, there arises the recombination between two loxPs in the construction and the region located between them is cut off therefrom as a cyclic molecule. Thus, the virus structural protein gene (or the foreign gene) is expressed for the first time. A large characteristic of the present invention resides in that two functions, i.e., the expression of a drug resistance marker gene and the expression of a virus structural protein gene (for example, VSV-G) after the treatment with the Cre recombinase are established by a single promoter with the use of the Cre/loxP system as described above. Therefore, the present invention makes it possible to prepare a clinically applicable vector having a high titer by using the Cre/loxP system even in a case where a retrovirus vector with a high titer can be hardly constructed at a high reproducibility due to the cytotoxicity, etc. of the desired foreign gene or virus structural protein gene.

Although the recombinase recognition sequences are inserted in the regular order in the DNA constructions (A) and (B), those having the recombinase recognition sequences inserted in the opposite order also fall within the scope of the present invention. In the case of the DNA construction (B), the packaging signal may be followed by a promoter or the polyA sequence following the drug resistance gene may be deleted. The present invention involves any DNA constructions carrying the constituents of the DNA construction (B) arranged in the order as defined above regardless of the presence of the promoter and the polyA sequence as described above. A DNA construction free from the polyA signal can serve as a virus vector DNA even when it is not treated with the Cre recombinase. Thus the expression of the foreign gene can be initiated by transferring the Cre recombinase after the transduction of the target cells therewith. By using a specific promoter, the post-transductive expression of the foreign gene can be specifically regulated. Although another DNA may be inserted between the above genes (DNA constructions) in the constitutions of the DNA constructions (A) and (B), the present invention involves any DNA constructions aiming at the same objects as those of the present invention and having the same arrangements as the ones defined above.

As the drug resistance gene, use can be made of a neomycin resistance gene, a puromycin resistance gene, a hygromycin resistance gene, etc. which have been commonly employed in the art. Preferable examples thereof include a drug resistance gene the function of which has been deteriorated by substitution, insertion or deletion in the base sequence in the coding region thereof, a drug resistance gene the translation efficiency of which has been lowered by substitution, insertion or deletion in the base sequence in the untranslated region thereof (i.e., low-efficient drug resistance genes) and a drug resistance gene the stability of the mRNA produced by which has been lowered (i.e., a short-lived transcript drug resistance gene). It is still preferable to use therefor a short-lived mRNA neomycin resistance gene which is a short-lived transcript drug resistance gene obtained by transferring an mRNA unstabilizing sequence (ARE: AU-rich element) observed in the 3'-untranslated region of c-fos gene (Chen, C. A., Shyu, A., Mol. Cell. Biol., 14, 8471–8482, 1994) into the 3'-untranslated region of a publicly known resistance gene.

Another large characteristic of the present invention resides in that use of such a devised drug resistance gene makes it possible to efficiently screen cells with particularly high expression from the promoter transferred normally into chromosomes and to further elevate the screening efficiency of prepackaging cells for preparing a vector with a high titer. In the present invention, use is made of a neomycin resistance gene which can be screened with the use of G418 (mfd. by Schering AG).

The negatively charged high-molecular weight substance to be used as a reinfection inhibitor for elevating the recovery yield of the pseudotyped retrovirus is not particularly restricted. Examples thereof include heparin, heparan sulfate and chondroitin sulfate. It is preferable to use heparin therefor.

The virus structural protein may originate in any virus without restriction. As an envelope for preparing a pseudotyped virus, it is preferable to use a VSV-G gene which is the sequence of the VSV-G (indiana) species containing the full-length translated region (Gallione, C. J., 46, 162–169, 1983).

The foreign gene is not particularly restricted, so long as it is a gene aiming at cell transfer for gene therapy. However, the process of the present invention with the use of the Cre/loxP system is particularly efficacious in the cases of cytotoxic proteins. This is because such a protein doesn't undergo expression before the treatment with the recombinase and after treating with the recombinase, the protein is expressed within a short period of time by the same promoter, which makes it possible to prepare a retrovirus vector before the cytotoxicity is exhibited.

The virus genome to be used in the present invention may be an arbitrary one, so long as it is a genome originating in a retrovirus. Preferable examples thereof include those originating in oncoviruses such as Moloney murine leukemia virus (MoMLV) and in lentiviruses such as human immunodeficiency virus (HIV).

Although use may be made of promoters commonly employed in the art as the promoter of the DNA construction (A), it is preferable to use one with a high titer capable of expressing a virus protein within a short period of time. As an example thereof, a CAG promoter reported by Niwa et al. may be proposed (Niwa, H., Yamamura, K., Miyazaki, J., Gene, 108, 193–200, 1991).

Although the polyA addition sequence is not particularly restricted, it is preferable to use one originating in a rabbit β-globin gene or the SV40 virus.

The cells into which the DNA constructions (A) and (B) are to be transferred may be arbitrary ones, so long as the gag and pol genes encoding structural proteins can be expressed therein. As a preferable example thereof, FLY cells (Cosset, et al., J. Viol., 69, 7430–7436, 1995) may be porposed.

The above-mentioned retrovirus gag, pol-producing cells having a DNA construction (A), in particular, those containing a VSV-G gene are useful in preparing prepackaging cells for the production of virus vectors, in particular, pseudotyped virus vectors. These cells are involved in the scope of the present invention. The retrovirus gag, pol-producing cells having a DNA construction (A) and a DNA construction (B) or a retrovirus vector DNA encoding a conventional type foreign gene transferred thereinto are useful as prepackaging cells containing a virus vector DNA for the production of retrovirus vectors, in particular, those of the pseudotypes. These cells are also involved in the scope of the present invention. Prepackaging cells for the production of retroviruses having ecotropic envelope proteins capable of exclusively transducing rodent cells or amphotropic envelope proteins capable of transducing various cells including human ones, namely, retrovirus gag-pol-env-producing cells having a DNA construction (B) transferred thereinto are useful as prepackaging cells containing a virus genome for the production of usual retrovirus vectors containing a desired foreign gene to be transferred. These prepackaging cells are particularly useful when the desired foreign gene to be transferred is a cytotoxic one. These cells are also involved in the scope of the present invention.

To transfer into cells a Cre recombinase expression system for making the Cre recombinase to act in the cells, use can be made of retrovirus vectors, adenovirus vectors, etc. A preferable example thereof is an adenovirus vector (JP-A 8-84589).

The present invention is largely characterized in that two functions, i.e., the expression of a drug resistance marker gene and the expression of VSV-G gene (or foreign gene) after the treatment with the Cre recombinase can be established by using a single promoter, and that the screening efficiency of prepackaging cells for preparing a vector with a high titer can be elevated by using deteriorated drug resistant marker. It is expected that the process of the present invention is effective particularly in a case where a retrovirus vector having a high titer can be hardly prepared at a high reproducibility due to the cytotoxicity etc. of a desired foreign gene, etc.

MODE FOR CARRYING OUT THE INVENTION

In the present invention, preparation of each DNA construction, handling of viruses and cells, etc. may be effected by well known methods commonly employed in the art. For example, use can be made of the procedures described in "Shin-seikagaku Jikken Koza, vol. 18, Saibo Baiyo Gijutsu" (1990), Tokyo Kagaku Dojin; "Idenshi Chiryo no Kiso Gijutsu", Yodosha (1996); and "Molecular Cloning. A Laboratory Manual", ed. by T. Manitis et al. (1989), Cold Spring Harbor Laboratory.

Next, a process for preparing a DNA construction (pCALNLG) having a drug resistance gene for inducing the expression of the VSV-G gene product by the Cre recombinase and a process for preparing another DNA construction (pCALNdLG) having a sequence transferred thereinto for making short-lived the transcript of the drug resistance gene contained in the former DNA construction (hereinafter referred to as the short-lived transcript sequence) will be described.

Figure 2:
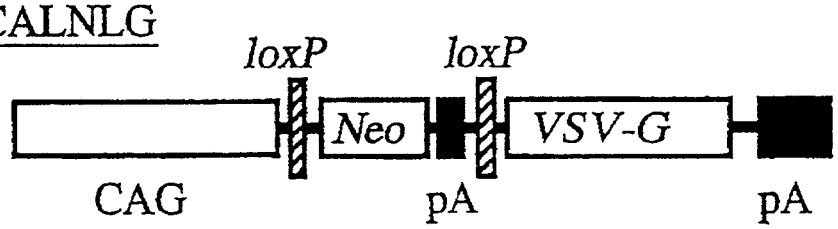
FIG. 2 shows the construction of pCALNLG and pCALNdLG.
Figure 2:
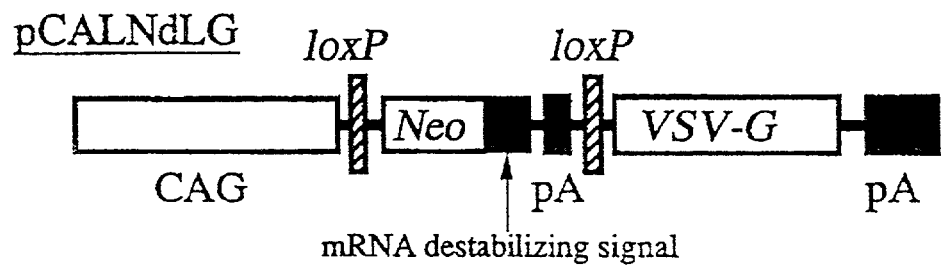

To prepare pCALNLG, the code sequence of the G protein of VSV (Indiana: serum type) (Rose, J. K., Cell, 30, 753–762, 1982) is inserted into the SwaI-cleavage site of pCALNLw which has been constructed by deleting a lacZ gene from pCALNZ (Kanegae, Y., et al., Nucl. Acids, Res., 23, 3816–3821, 1995) and transferring the SwaI-cleavage site thereinto and wherein the loxP sequences are located on both sides of the neomycin resistance gene in the regular order (FIG. 2).

To transfer the short-lived mRNA sequence into the 3'-untranslated region of the drug resistance gene in pCALNLG, a sequence of 414 bps which is the short-lived mRNA sequence of chicken c-fos (AU Rich Element: ARE) having been cleaved with ClaI and BglII (the BglII site having been blunt-ended with klenow fill in) is inserted into the NspV, ClaI-cleavage sites (the ClaI site having been blunt-ended by creating an NruI-site by blunting with klenow fill in and then cleaving with by NruI) by using the adhesion of the NspV-site to the ClaI-sites, thus constructing pCALNdLG (FIG. 2).

Figure 3:
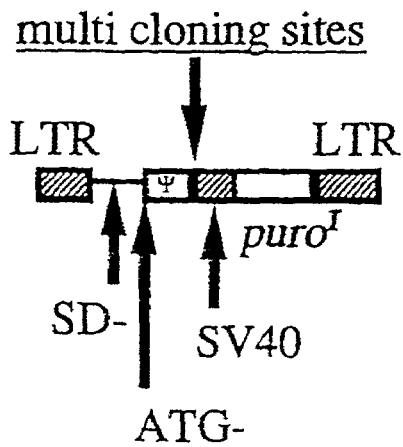
FIG. 3 shows the construction of pBabe and pBabeloxpuro.
Figure 3:
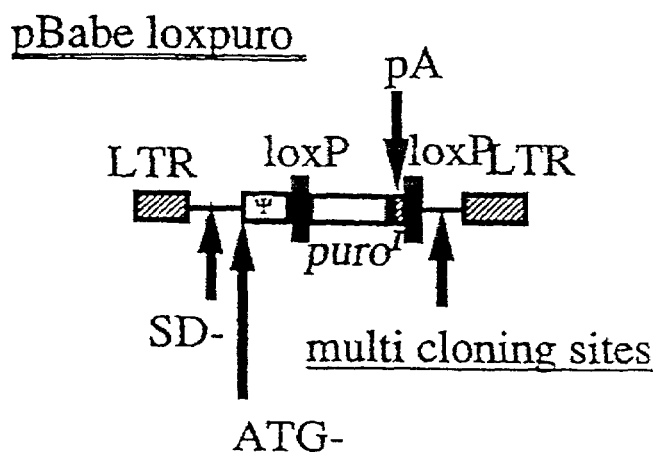

As a retrovirus vector DNA originating in Moloney murine leukemia virus (MoMLV) for transferring a foreign gene, use is made of pBabe (Morgenstennm, J. P. and Hartmut, L., Nucleic Acids Res., 18, 3587–3596, 1990), etc. FIG. 3 shows the one prepared and used as a retrovirus genome.

The retrovirus vector DNA pBabe loxpuro for cutting off the drug resistance gene as a cyclic molecule by treating with the Cre recombinase to thereby initiate the expression of the foreign gene is constructed in the following manner. As a multicloning site for inserting a foreign gene, the following oligo DNA is designed and ordered. Thus, this DNA is purchased from Greiner Japan. Restriction enzyme recognition sites are underlined.

```
5'-tcgac gc agatct cacgtg atttaaat at-3'   (SEQ ID
                                            NO:1)

SalI  BglII   PmlI SwaI    ClaI

3'-  g cg tctaga gtgcac taaattta tagc-5'   (SEQ ID
                                            NO: 2)
```

DNA containing the puromycin resistance gene and the SV40 polyA signal is cut off from pPUR (mfd. by GIBCO) with HindIII and BamHI and then inserted into the HindIII, BamHI-sites of pBS246 (mfd. by GIBCO) which is a plasmid for integrating the loxP sequence. Next, a fragment loxP/puromycin resistance gene/SV40 polyA/loxP sequence is cut off therefrom with EcoRI and ScaI and blunt-ended by a Klenow fragment to give a loxpuro insert. Separately, the SV40 promoter and the drug resistance gene are deleted from pBabe with the use of SalI and ClaI and the above-mentioned oligo DNA for transferring the multicloning site is inserted thereinto. Then the loxpuro insert is inserted into the site having been cleaved with SnaBI to give pBabe loxpuro. At the same time, construction is made of another DNA construction (pBabe loxpuroDpA) which is free from the SV40 polyA signal and thus can serve as a virus vector DNA without the treatment with the Cre recombinase so as to initiate the expression of the foreign gene when it transduces target cells followed by the transfer of the Cre recombinase thereinto.

The nlslacz cut off from pCALNZ (Kanegae, Y. et al., Nucl. Acids, Res., 23, 3816–3821, 1995) is inserted into pBabe or pBabe loxpuro and then employed in the preparation of a retrovirus genome with β-galactosidase (nlslacz) having a nuclear transport signal for measuring the virus titer.

The virus titer is measured in the following manner. One day before the infection, rat fibroblasts 3Y1 are transferred into a 96-well plate to give a cell density of $1.5 \times 10^{+3}/96$ wells. Samples are thawed and diluted with the liquid culture medium at various levels. Then the rat fibroblasts 3Y1 are transduced therewith together with 0.5 μm/96 wells of polybrene. After three days, the infected cells are fixed with 1.25% glutaraldehyde and the lacZ-transduced cells are stained by using X-gal in accordance with the method described above. The colonies thus stained blue are counted and it is confirmed that the colony count varies depending on the dilution level, thus calculating the titer. The titer is expressed in the number of the infectious units (hereinafter referred to simply as i.u.) per ml, namely, i.u./ml.

The VSV-G gene product and MLV gag p12 are immunologically stained by using VECTASTAIN (mfd. by VECTOR) in the following manner. The cells are fixed in PBS containing 3% of p-formaldehyde and 0.1% Triton X-100 at room temperature for 15 minutes. After washing with PBS twice, primary antibody solutions diluted 1,000- to 3,000-fold are prepared by using Hank's buffered salt solution (HBSS) containing goat serum and bonded thereto at room temperature for two hours. After washing with PBS twice, a biotin-labeled secondary antibody against mice, which is the primary antibody-producing animal, is diluted 1,000-fold with HBSS containing caprine serum and bonded at room temperature for 30 minutes. Subsequently, staining is effected according to the manufacturer's instructions of VECTASTAIN.

EXAMPLES

To further illustrate the present invention in greater detail, and not by way of limitation, the following Examples will be given.

Example 1

Transfer of pCALNLG into FLY Cells and Primary Screening of Prepackaging Cell Lines Inducing the Expression of VSV-G Gene Product A DNA construction pCALNLG (FIG. 2) having a neomycin resistance gene for inducing the expression of the VSV-G gene product by the Cre recombinase was transfected in the following manner into FLY cells (Cosset, et al., J. Virol., 69, 7430–7436, 1995) capable of expressing the gag and pol gene products of MoMLV stably.

10 to 30 µg of pCALNLG was transfected into FLY cells, which had been transferred on the previous day to give a density of $5\times10^5$ cells/10 cm dish, by the calcium phosphate method (Chen, C. and Okayama, H., Mol. Cell. Biol. 7, 2745–2752, 1987). On the next day, the calcium phosphate was eliminated and the cultured cells were divided one or two days thereafter. On the next day, 1 mg/ml of G418 (mfd. by GIBCO) which is a neomycin derivative was added thereto to screen stable strains. The screening was continued for about 14 days. When G418-resistant colonies attained such a size as allowing fishing, the colonies were individually transferred into a 96-well plate by using a cloning cylinder and then cultured therein.

Each colony was divided into two. One of these sections was infected with an adenovirus (AxCANCre) for the expression of the Cre recombinase (Kanegae, et al., Nucleic Acids Res., 23, 3816–3821, 1995) at a multiplicity of infection (hereinafter referred to simply as m.o.i.) of 30. Thus the Cre recombinase was transferred thereinto and G418 was removed from the liquid culture medium. Another section of the colony was not subjected to any treatment but cultured as such to store the cells in liquid nitrogen. Three days after the infection, the expression of the VSV-G gene product in the one infected with AxCANCre was detected by the above-mentioned immunological staining method with the use of a VSV-G antibody (P5D4, Sigma V5504). Among 11 clones thus obtained, two (PtG-L1 and PtG-L2) showed the expression of the VSV-G gene product under the action of AxCANCre. When these colonies were compared with each other, PtG-L1 showed much stronger staining than PtG-L2. On the other hand, none of the clones not infected with AxCANCre showed any expression of the VSV-G gene product.

Example 2

Detection of VSV-G Gene Product Produced by PtG-L1 Cells by Western Blotting Method The VSV-G gene product produced by PtG-L1, i.e., the prepackaging cells strongly stained in Example 1, was detected by using the anti-VSV-G antibody (P5D4) recognizing the C-terminal part thereof in the following manner.

Figure 4:
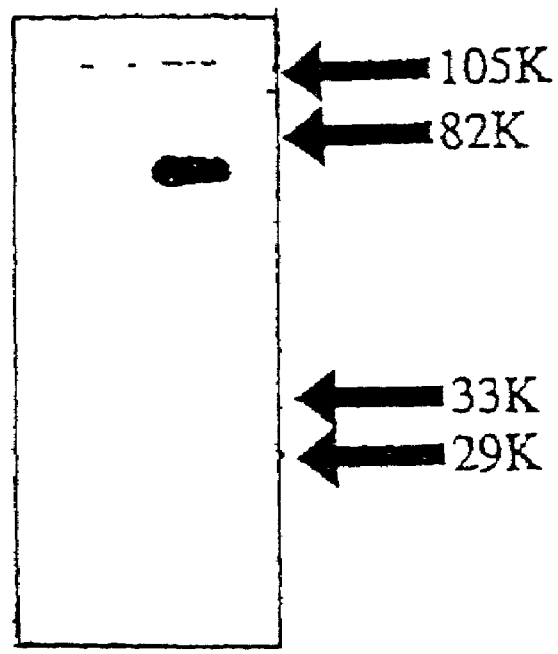
FIG. 4 shows the detection of VSV-G by the Western blotting method.

The PtG-L1 cells were transferred into two dishes (10 cm) to give a density of $5\times10^5$ cells/dish. On the next day, the cells in one dish were infected with AxCANCre at an m.o.i. of 30, while those in another dish were not infected. After four days, the cell constituents were solubilized with 500 µl of a sample buffer (61.2 mM Tris/HCl, pH=6.8, 1.6% SDS, 2.5% β-mercaptoethanol, 9.8% glycerol), then treated at 100° C. for 5 minutes and stored at −20° C. The protein contained in the sample thus obtained was determined by using a protein assay solution (mfd. by BIORAD) and SDS-PAGE was carried out in such a manner as to give 20 µg of the protein per lane. The electrophoretic gel was electrotransferred onto Immobilon (mfd. by Millipore) and bonded to a primary antibody which was the VSV-G antibody (P5D4, Sigma V5504) diluted 3,000-fold and a secondary antibody which was a biotin-labeled antibody against mice IgG, which were the primary antibody-immune animal, diluted 1,000-fold. Then detection was performed by using an ECL kit (mfd. by Amersham). As a result, the sample treated with AxCANCre showed a band at 70 kDa which was seemingly assignable to the VSV-G gene product, while the uninfected one showed no band. These results agreed with the results of the immunological staining. Namely, the sample not treated with AxCANCre showed no expression of the VSV-G gene product while the Cre recombinase transferred by AxCANCre induced the expression of the VSV-G gene product. FIG. 4 shows the results.

Example 3

Transfer of Virus Vector DNA into PtG-L1 and Determination of Virus Production by Cre Recombinase Eleven clones which had not been subjected to any treatment but been cultured as such as described in Example 1 were stored in liquid nitrogen and a retrovirus vector DNA encoding β-galactosidase (lacZ) was transferred into a portion of these cells via transduction of amphotropic retrovirus encoding nlslacz. After confirming that the retrovirus genome encoding lacZ had been transferred into most of the cells by X-gal staining, each clone was divided into two. One section was not infected but cultured as such, while another section was infected with AxCANCre to thereby induce the expression of the VSV-G gene product. Subsequently, the liquid culture medium was replaced by a fresh one at intervals of about three days until the day before the recovery of the virus. On the next day, the culture supernatant was recovered and centrifuged at 3,000 rpm for 30 minutes. The supernatant thus obtained was stored at −80° C. as a virus stock. When the titer of each clone was measured by using rat fibroblasts 3Y1 with the use of the expression of the lacZ gene as an indication, the virus was detected from four clones infected with AxCANCre including the above-mentioned PtG-L1 and PtG-L2. On the other hand, those not treated with AxCANCre showed no production of the virus. Two clones in which the expression of the VSV-G gene product could not be confirmed showed low titers and the virus production thereof depended on AxCANCre. These results indicated that the VSV-G gene product was expressed in these clones in such a small amount that it could not be detected at the sensitivity of the immunological staining employed. Among these colonies, PtG-L1 having the Cre recombinase transferred thereinto showed a maximum virus productivity of $4\times10^3$ i.u./ml. Since the three clones other than PtG-L1 showed virus productivities of less than 100 i.u./ml, the subsequent studies were focused on PtG-L1 to clarify its properties.

Example 4

Properties of Envelope Protein of Virus Vector Produced by PtG-L1

It was expected that the envelope of the virus produced by PtG-L1 might be VSV-G (Indiana type) originating in pCALNLG, since the virus was produced depending on AxCANCre. To confirm this point, an anti-VSV-G antibody (Indiana type ATCC VR-1238AF) was purchased from ATCC and the following experiment was carried out for inhibiting the transduction.

A virus sample produced by treating PtG-L1 with AxCANCre was mixed with 1/10 time (v/v) as much the antibody and reacted at 4° C. for one hour. Next, the effect on the infection was examined by the above method by using 3Y1 with the use of the expression of the lacZ gene as an indication (Table 1). As a negative control, use was made of an anti-VSV-G antibody not binding to the Indiana type VSV-G (New Jersey type ATCC VR-1238AF). When the anti-VSV-G antibody (Indiana type) was used, the infection was completely inhibited at a level of 1/10. This effect was also observed at a level of 1/1,000. In contrast, the negative control anti-VSV-G antibody (New Jersey type) exerted no effect on the infection regardless of the dilution level. These facts indicated that the envelope of the virus produced by PtG-L1 was VSV-G (Indian type) as expected.

TABLE 1

Infectivity titer (i.u./ml) of virus produced by PtG-L1 after treating with anti-VSV-G antibody

| Antibody dilution level/<br>Antibody | 1/10 | 1/100 | 1/1000 | No<br>anti-body |
|---|---|---|---|---|
| anti-VSV-G antibody<br>(Indiana type) | <10 | $3.0 \times 10^2$ | $1.4 \times 10^3$ | $3.3 \times 10^3$ |
| anti-VSV-G antibody<br>(New Jersey type) | $3.2 \times 10^3$ | $2.8 \times 10^3$ | $2.8 \times 10^3$ | $3.3 \times 10^3$ |

Example 5

Elimination of Neomycin Resistance Gene from Chromosome after the Introduction of Cre Recombinase After transferring the Cre recombinase into PtG-L1 by the infection with AxCANCre, G418 was added to the liquid culture medium in one culture while G418 was eliminated from the liquid culture medium in another culture. Then these cultures were compared with each other in viable count. After nine days, the viable count of the culture to which G418 had been added was reduced to less than 5% of that of the culture from which G418 had been eliminated. It was thought that the neomycin resistance gene would be continuously expressed so long as it existed in chromosomes but its expression would be ceased when it was eliminated from the chromosomes as a cyclic DNA. Accordingly, it was considered that the fact that the neomycin resistance disappeared in PtG-L1 infected with AxCANCre indicated that the neomycin resistance gene had been eliminated from the chromosome by the Cre recombinase.

Example 6

Stability of pCALNLG Gene in PtG-L1

Figure 5:
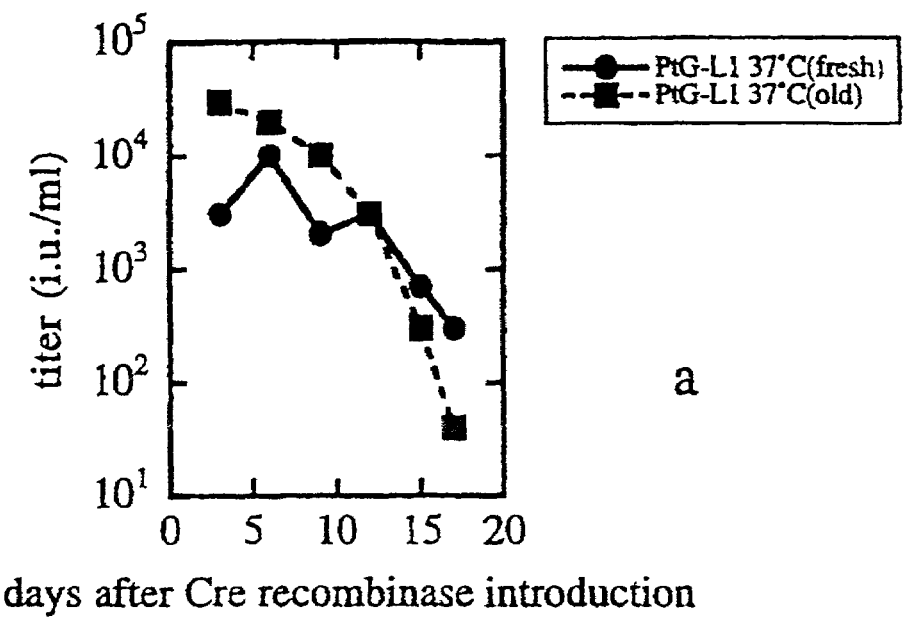
FIG. 5 shows the stability of PtG-L1 as prepackaging cells.
Figure 5:
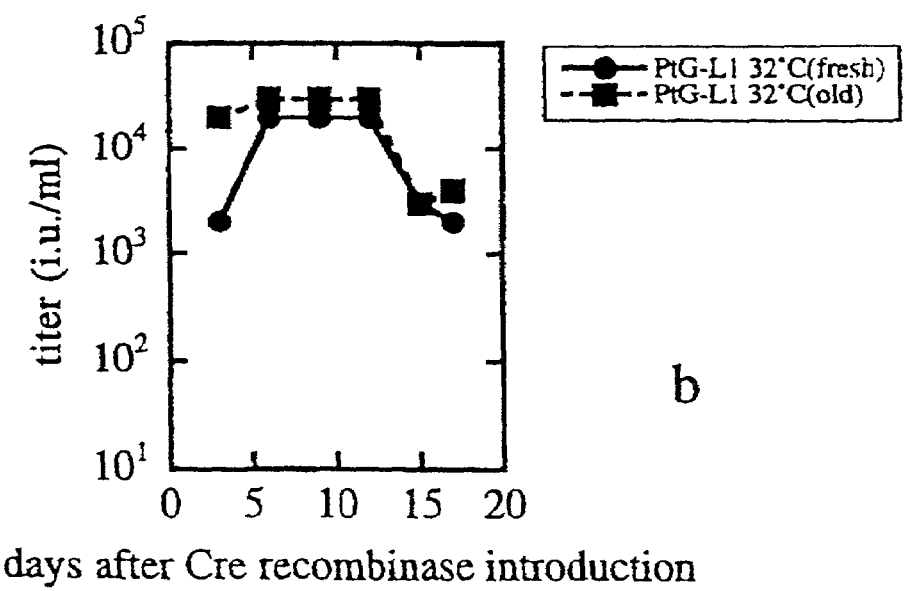

To examine whether or not the pCALNLG gene was sustained in PtG-L1 stably, the following experiment was carried out by using PtG-L1lacZ which had been prepared by transferring the lacZ vector DNA employed in Example 3 into PtG-L1 and then stored in liquid nitrogen. The Cre recombinase was transferred by using AxCANCre at an m.o.i. of 30 into PtG-L1lacZ-1 newly taken out from liquid nitrogen and thawed and PtG-L1lacZ-2 which had been continuously cultured for two months without transferring the Cre recombinase. After continuously culturing for two months, the cell count of PtG-L1lacZ-2 became $8.7 \times 10^{13}$ times as high as that of the initiation of the culture. Then the procedure of Example 1 was followed by using the liquid culture medium as a virus stock and thus the virus productivity was measured by using 3Y1 with the use of the expression of the lacZ gene as an indication. FIG. 5a shows the data of the cells which had been cultured at 37° C. starting with the third day after the infection with AxCANCre, while FIG. 5b shows the data of those cultured at 32° C. Although PtG-L1lacZ-1 showed somewhat low productivities on the third day after the AxCANCre-infection, the productivities thereafter were almost comparable to those of ptG-L1lacZ-2. It was therefore considered that the pCALNLG and gag, pol genes were sustained stably in PtG-L1.

Example 7

Examination of Optimal Conditions for Virus Production by PtG-L1

The results of Examples 2 to 4 suggested that PtG-L1 had the expected properties. To find the optimum conditions for the virus production, the following experiment was carried out.

The conditions for the virus production by PtG-L1 were examined from the viewpoints (a) to (c) as specified below and changes in the titer of the virus thus produced were monitored with the passage of time:

(a) m.o.i. of the infection with AxCANCre: 0, 3, 10, 30, 100, 300, 1,000 and 3,000 (3, 10, 1,000 and 3,000 being employed only in some cases);

(b) cell count at infection: $1.5 \times 10^4$, $4.5 \times 10^3$ and $1.5 \times 10^3$ per 48 wells; and (c) culture temperature starting with the third day after the AxCANCre-infection: 32 and 37° C.

The effect of each condition on the virus titer was examined by the above-mentioned method by using 3Y1 with the use of the expression of the lacZ gene as an indication. Thus the following results were obtained.

(a) When the m.o.i. of the infection with AxCANCre was 300 or above, a potent toxicity of adenovirus was exhibited and thus the virus titer was sustained at a low level until viable cells increased. The maximum productivity was achieved at an m.o.i. of about 30 to 100. No virus production was observed under every condition in the cells not infected with AxCANCre (i.e., m.o.i.=0).

(b) The cell count at the infection exerted no large effect on the virus productivity per cell. When there were a small number of cells at the initiation, only a low virus productivity was observed in the early stage but a virus productivity comparable to the one in the case with a large initial cell count could be established after the cell count was increased by continuing the culture.

(c) When the maximum titer was employed as an indication, no large difference was observed between the culture effected at 37° C. desirable for cell proliferation and the one at 32° C. at which amphotropic viral particles would be more stable (Kotani, H., et al., Hum. Gene. Ther., 5, 19–28, 1994). A relatively stabilized virus production was observed at 32° C.

Figure 6:
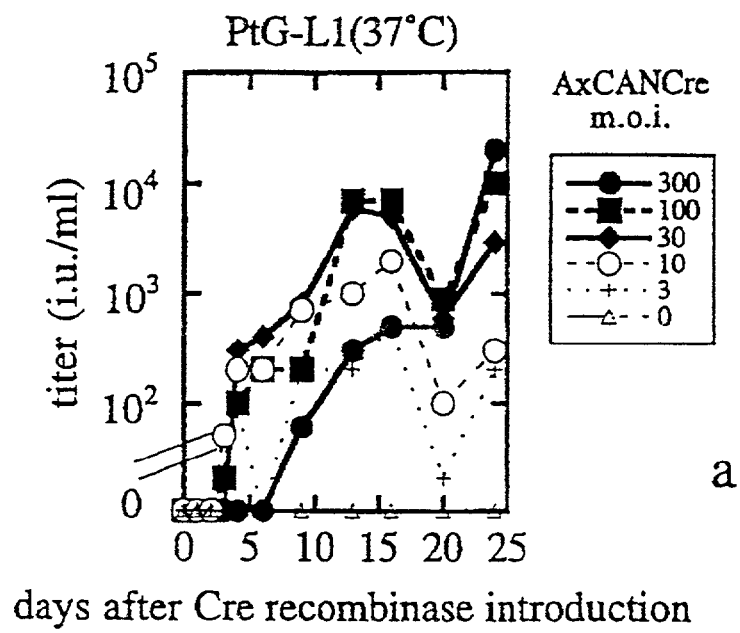
FIG. 6 shows a change in the virus productivity of PtG-L1 with the passage of time.
Figure 6:
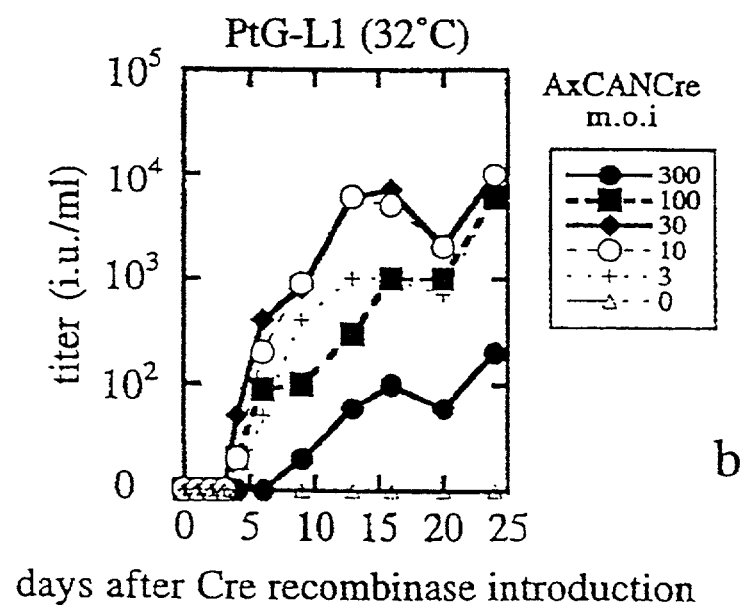

The maximum virus productivity was $2 \times 10^4$ i.u./ml (initial cell count=$4.5 \times 10^3$ cells/48 wells, m.o.i.=3,000, the 22nd day after the infection, 37° C.). FIG. 6a shows a change in the virus productivity with the passage of time under the conditions specified above, while FIG. 6b shows one under the same conditions but the temperature was 32° C. In the case where the maximum productivity was achieved, the cell count was first decreased due to the cytotoxic effect of the adenovirus virus, since the cells were infected with AxCANCre at a high m.o.i. However, the cells reached confluence on the 22nd day.

Example 8

Detailed Analysis on the Genotype of PtG-L1

As discussed above, a stable cell line PtG-L1 could be established by transfecting pCALNLG into FLY cells. The virus production completely depended on the transfer of the Cre recombinase and the envelop of the virus thus produced was VSV-G (Indiana type). Although the resultant virus showed the anticipated properties in qualities, the virus productivity which had been $2 \times 10^4$ i.u./ml at the maximum level was still insufficient quantitatively.

As described above, PtG-L1 showed only an insufficient virus productivity. Accordingly, the following experiments (a) to (c) were effected to examine the reason for this insufficiency:

(a) to clarify whether or not the VSV-G gene product was not expressed in some of the PtG-L1 cells; or whether or not the Cre recombinase transfer efficiency by the adenovirus suffered from some problems;

(b) to confirm the stable sustenance of lacZ by the X-gal staining method; and (c) to confirm the stable sustenance of MLVgag by the immunological staining method.

PtG-L1lacZ, the FLY cells in which PtG-L1lacZ originated, and 3Y1 cells employed as a negative control were pipetted into 48-well plates (3 plates for each) at densities of $1.5 \times 10^4$ (PtG-L1 and FLY) and $5 \times 10^3$ (3Y1) respectively. On the next day, these cells were infected with AxCANCre at an m.o.i of 0 or 30. By fixing after five days, the following results were obtained.

(a) VSV-G was immunologically stained by the above-mentioned method. As a result, FLY and 3Y1 were never stained regardless of the AxCANCre-infection. In contrast, the PtG-L1lacZ cells infected with AxCANCre were stained in almost entire populations. These results suggested that PtG-L1 was a uniform cell clone and thus the contamination with cells showing no expression of the VSV-G gene product might not affect the virus production. By the gene transfer with the use of the adenovirus vector, the Cre recombinase could be transferred into almost all cells and it was suggested that transfer was followed by the recombination induced by the Cre recombinase.

(b) To confirm the stable sustenance of the virus vector DNA encoding lacZ, PtG-L1lacZ was stained with lacZ by the method described above. As a result, all of the cells were stained with lacZ. Based on this result, it was assumed that the virus vector DNA encoding lacZ was sustained stably in PtG-L1lacZ and thus did not affect the virus production.

(c) Hybridomas (CRL-1890) capable of producing an antibody against MLVgagp12 were purchased from ATCC and MLVgagp12 was detected by the above-mentioned method with the use of a monoclonal antibody prepared from mouse ascites fluid. As a result, the 3Y1 cells were never stained, while the FLY cells and PtG-L1lacZ cells all showed staining of MLVgagp12. Based on these results, it was considered that MLVgag was sustained stably in PtG-L1lacZ and thus did not affect the virus production. Since gag and pol had the same transcriptive initiation point, it was considered that pol was sustained stably therein, too.

These results suggested that gag, pol and env (VSV-G) constituting the virus and the virus vector DNA encoding lacZ were sustained each stably in PtG-L1 and these facts might not affect the virus production.

When PtG-L1 was compared by the VSV-G immunological staining method after the transfer of the Cre recombinase with the cell lines with little virus production other than PtG-L1 as described in Example 1, PtG-L1 was stained much strongly. Namely, the expression dose of the VSV-G gene product correlated to the virus titer.

Based on these results, it was considered that the insufficient virus productivity of PtG-L1 as described in Example 6 might be caused by the fact that the expression level of the VSV-G gene product was still insufficient for the production of a virus having a high titer.

To more efficiently screen a stable cell line with a high expression level of the VSV-G gene product, therefore, the following DNA construction was devised and constructed.

A short-lived mRNA sequence originating in c-fos was transferred into the 3'-untranslated region of a drug resistance gene to thereby reduce the productivity of the resistance gene, thus relatively efficiently screening a cell line with a high expression level from the CAG promoter. After transferring the Cre recombinase, the VSV-G gene was transcribed by the same promoter as the one for the resistance gene. Thus, it was expected that the cell line screened by this DNA construction would have a high productivity of the VSV-G gene product. As described above, a DNA construction (pCALNdLG) was constructed by transferring the short-lived mRNA sequence originating in c-fos into the 3'-untranslated region of the drug resistance gene. Then the following experiment was effected while comparing this DNA construction with pCALNLG as described above.

Example 9

Effect of pCALNdLG Containing Short-Lived mRNA Sequence and Primary Screening of Prepackaging Cell Line with the Expression of VSV-G Gene Product By the method described in Example 1, 10 to 30 μg of pCALNLG or pCALNdLG was transfected into FLY cells and clones showing the stable expression were transferred into 96-well plates by using G418.

Each colony was divided into two. One section was infected with AxCANCre at an m.o.i. of 10 to thereby transfer the Cre recombinase thereinto. Then G418 was eliminated from the liquid culture medium. On the other hand, another section was not subjected to any treatment but continuously cultured as such to give a cell stock. Three days after the infection, the VSV-G gene product thus produced in the adenovirus-infected cells was detected by the immunological staining method as described above with the use of a VSV-G antibody (P5D4, Sigma V5504). After independently effecting a transfection experiment thrice, the cells transfected with pCALNdLG showed a number of the G418-screened clones about ⅓ time as large as that of the cells transfected with pCALNLG. It was thus suggested that more stringent screening was carried out by making the mRNA of the drug resistance gene short-lived. As the results of another transfection experiment conducted twice independently, it was found out that one clone among 25 clones transfected with pCALNLG showed the expression of VSV-G comparable or superior to that of PtG-L1, while three clones among 11 clones transfected with pCALNdLG carrying the short-lived mRNA drug resistance gene showed the VSV-G expression comparable or superior thereto. No VSV-G gene product was detected in all of the clones not infected with the adenovirus for the expression of the Cre recombinase. These results indicated that by making the mRNA of the short-lived drug resistance gene, more stringent screening could be carried out and thus clones with the high expression of the VSV-G gene product induced by the recombinase could be screened at an elevated efficiency. Accordingly, the same procedures for the transfection and the detection of the VSV-G gene product were effected by using pCALNdLG alone. Thus, 25 clones with the high expression of the VSV-G gene product depending on the Cre recombinase were obtained among 225 clones. Since none of the cells transfected with pCALNLG therein showed the expression of the VSV-G gene product in a dose exceeding that of PtG-L1, PtG-L1 was employed in the subsequent studies as a typical example of the stable cell line of pCALNLG.

Example 10

Transfer of Retrovirus Vector DNA into Prepackaging Cell Line and Measurement of the Pseudotyped Virus Production in each Clone by Cre Recombinase One clone (PtG-L1) transfected with pCALNLG and 25 clones transfected with pCALNdLG, which had been obtained as a clone capable of expressing the VSV-G gene product at a high level depending on the Cre recombinase, were stored in liquid nitrogen. To examine the virus-producing activity, a portion of each clone was transduced with a virus having a β-galactosidase (lacZ) gene in its vector DNA to give prepackaging cells containing the virus vector DNA of the 26 clones in total. When examined in accordance with the staining method described above, the vector could be transferred into each clone at an efficiency of almost 100%. Subsequently, each clone was divided into two and infected with AxCANCre at an m.o.i. of 10. The day of the infection was defined to be the day 0. Both of the sections were cultured at 37° C. until the day 2 and then treated with the recombinase. After the day 3, one of the sections was cultured at 37° C. continuously, while another was cultured at 32° C. at which viral particles might be more stable. The virus titer was measured by replacing the liquid culture medium by a fresh one one day before the collection at intervals of about three days. Each virus sample thus taken up was centrifuged at 3,000 rpm for 30 minutes and the supernatant was stored at −80° C. until immediately before the analysis. The titers of these virus samples were measured in accordance with the method as described above by using 3Y1 with th1e use of the expression of the lacZ gene as an indication.

Figure 7:
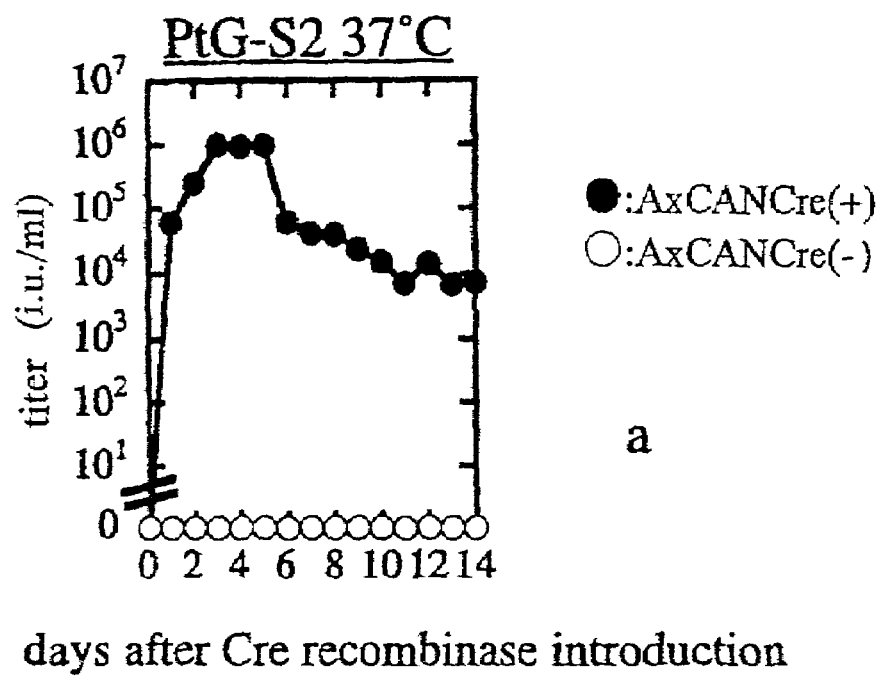
FIG. 7 shows a change in the pseudotyped retrovirus productivity of PtG-S2 with the passage of time.
Figure 7:
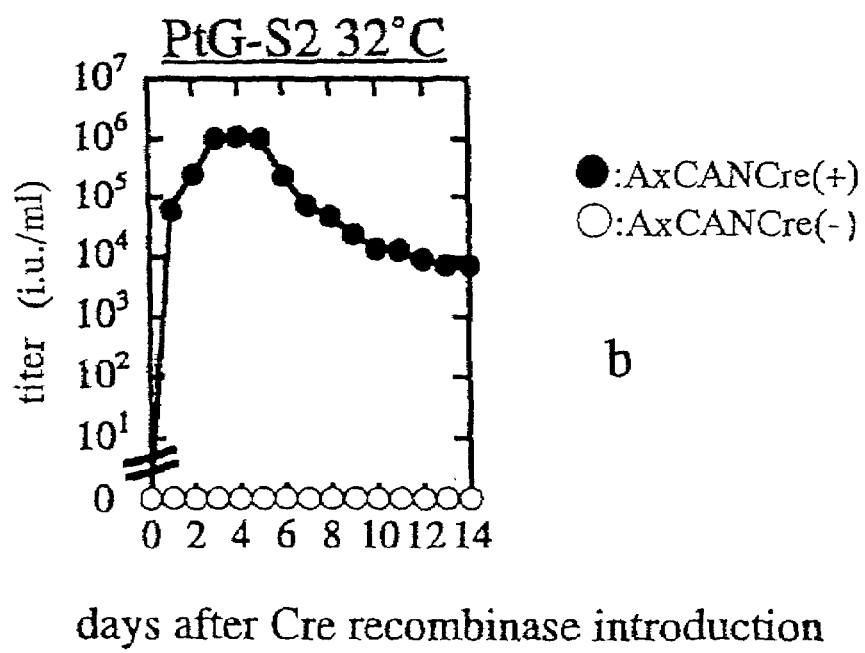
Figure 8:
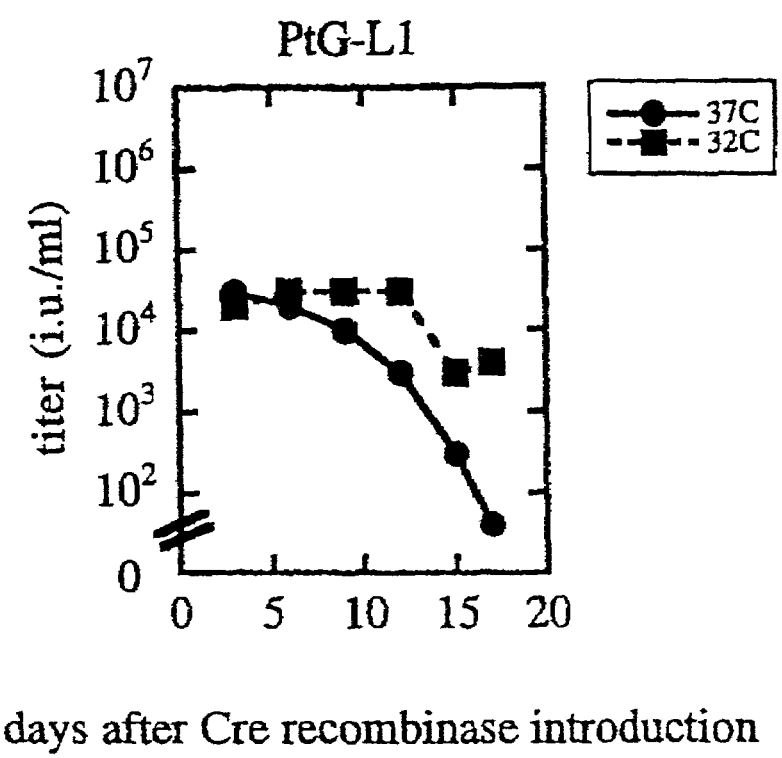
FIG. 8 shows a change in the pseudotyped retrovirus productivity of PtG-L1 with the passage of time.

When the 26 clones thus examined were classified depending on the maximum titer, one clone showed a maximum titer of $10^6$ i.u./ml or above, eight clones showed that of from $10^5$ i.u./ml to less than $10^6$ i.u./ml, 14 clones showed that of from $10^4$ i.u./ml to less than $10^5$ i.u./ml, and three clones showed that of from $10^3$ i.u./ml to less than $10^4$ i.u./ml. The production of the virus was observed in none of the cells into which the Cre recombinase had not been transferred. FIGS. 7 and 8 show the changes in the virus productivity of one clone (PtG-S2) showing the highest titer among those transfected with pCALNdLG and another clone (PtG-L1) transfected with pCALNLG.

Example 11

Properties of Envelope Proteins of Virus Vectors Produced by PtG-L1, PtG-S2 and PtG-S1

To identify the envelope proteins of the virus vectors thus formed, it was examined whether or not the infection of the virus samples produced by the three clones screened in Example 9 was neutralized by the anti-VSV-G antibody (Indiana type). Namely, each sample was reacted with the antibody by the method described in Example 2. Then the effect on the infection was examined in accordance with the above-mentioned method by using 3Y1 with the use of the expression of the lacZ gene as an indication. Table 2 shows the results.

The anti-VSV-G antibody (Indiana type) completely inhibited the viral infection with all of the viruses produced by the above clones. In contrast thereto, anti-VSV-G (New Jersey type) caused no change. It was thus clarified that the viruses induced by transferring the Cre recombinase were pseudotyped viruses having the VSV-G (Indiana type) originating in pCALNLG or pCALNdLG as the envelope protein.

TABLE 2

Effects (i.u./ml) of virus samples on infection examined by incubating with antibody
(virus samples being incubated with 1/10 time as much antibody)

| Antibody/ Clone | Anti-VSV-G antibody (Indiana type) | Anti-VSV-G antibody (New Jersey type) | No antibody |
|---|---|---|---|
| PtG-L1 | <10 | $2.0 \times 10^3$ | $2.0 \times 10^3$ |
| PtG-S1 | <10 | $6.0 \times 10^4$ | $6.0 \times 10^4$ |
| PTg-S2 | <10 | $1.0 \times 10^4$ | $1.0 \times 10^4$ |

Example 12

Analysis on Neomycin Resistance Gene Product and VSV-G Gene Product Produced by Prepackaging Cells by Western Blotting Method and Effects of Short-Lived mRNA Sequence on the Yields of these Products The following experiment was carried out to examine changes in the yields of the neomycin resistance gene product and the VSV-G gene production before and after transferring the Cre recombinase into the prepackaging cells.

Figure 9:
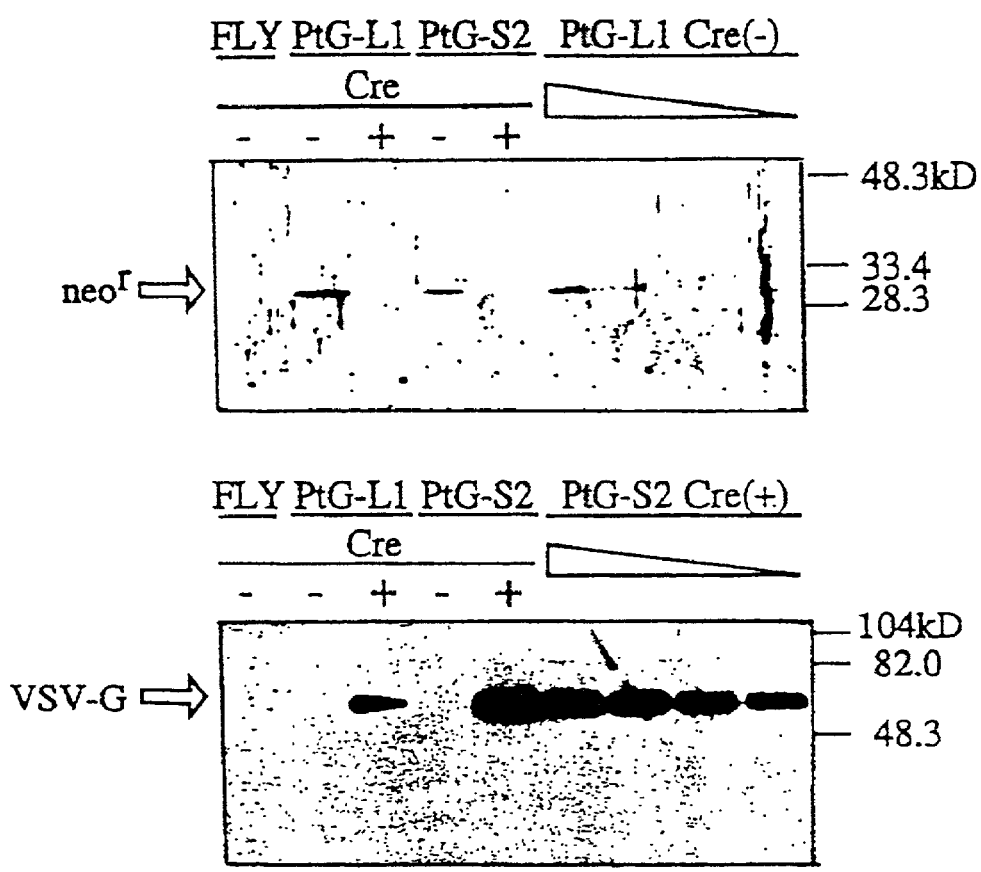
FIG. 9 shows an analysis on a change in protein synthesis determined by the Western blotting method before and after transferring the Cre recombinase.

By using PtG-L1 and PtG-S2 cells containing the MLV vector DNA encoding lacZ, protein samples were prepared under the introduction of the Cre recombinase (after transferring) and without introducing the Cre recombinase (i.e., corresponding to the state before transferring) similar to Example 2 followed by Western blotting (FIG. 9). To detect the neomycin resistance gene product, use was made of an anti-neomycin resistance gene product (5Prime to 3Prime sha/Funakoshi) diluted 1,000-fold and a biotin-labeled anti-rabbit (i.e., the primary antibody immune animal) IgG antibody diluted 1,000-fold as a secondary antibody.

In the detection pattern of the neomycin resistance gene (FIG. 9a), both of PtG-L1 and PtG-S2 into which no Cre recombinase had been transferred showed bands (20 µg per lane) The bands of PtG-S2 were less than those of PtG-L1. Compared with the bands of the PtG-L1 samples serially diluted 2-fold [PtG-L1 Cre (−); 10, 5, 2.5 and 1.25 µg/lane from right to left], it was estimated that the yield of the neomycin resistance gene product produced by PtG-S2 corresponded to about 1/3 of the yield thereof produced by PtG-L1.

In the detection pattern of the VSV-G gene product (FIG. 9b), only the cells into which the Cre recombinase had been transferred showed bands in both of PtG-L1 and PtG-S2 (20 µg per lane). The fact that the cells into which no Cre recombinase had been transferred showed no band agreed with the result of Example 10 wherein no virus was detected from the cells into which no Cre recombinase had been transferred. Compared with the bands of the PtG-S2 samples serially diluted 2-fold [PtG-S2 Cre (+); 10, 5, 2.5 and 1.25 µg/lane from right to left], it was estimated that the yield of the VSV-G gene product produced by PtG-S2 was about 20 times larger than that of PtG-L1.

These results indicated that the expression shifted from the neomycin resistance gene product to the VSV-G gene product by introducing the Cre recombinase both in PtG-L1 and PtG-S2 as expected. PtG-L1 and PtG-S2 respectively had pCALNLG and pCALNdLG as shown in FIG. 2. Namely, the difference between them resided only in the presence of the short-lived mRNA sequence. Since the neomycin resistance gene product and the VSV-G gene product were transcribed by the same promoter (shown by the arrow in FIG. 1), the production of the VSV-G gene product from the neomycin resistance gene product by PtG-S2 at an efficiency about 30 times higher than that of PtG-L1 was caused by the fact that mRNA of the transcribed neomycin resistance gene would be more quickly degraded in PtG-S2 by the short-lived mRNA sequence. It was also explicable thereby that the clones with high VSV-G expression could be screened at a high efficiency by using G418 in Example 9.

Example 13

Analysis on Changes in VSV-G Expression Units before and after Transferring Cre Recombinase by Southern Blotting Southern blotting was carried out by the method described in "Mode for Carrying Out the Invention" herein to examine changes in the VSV-G expression units (pCALNLG, pCALNdLG) transferred into the prepackaging cells via transfection before and after transferring the Cre recombinase.

Figure 10:
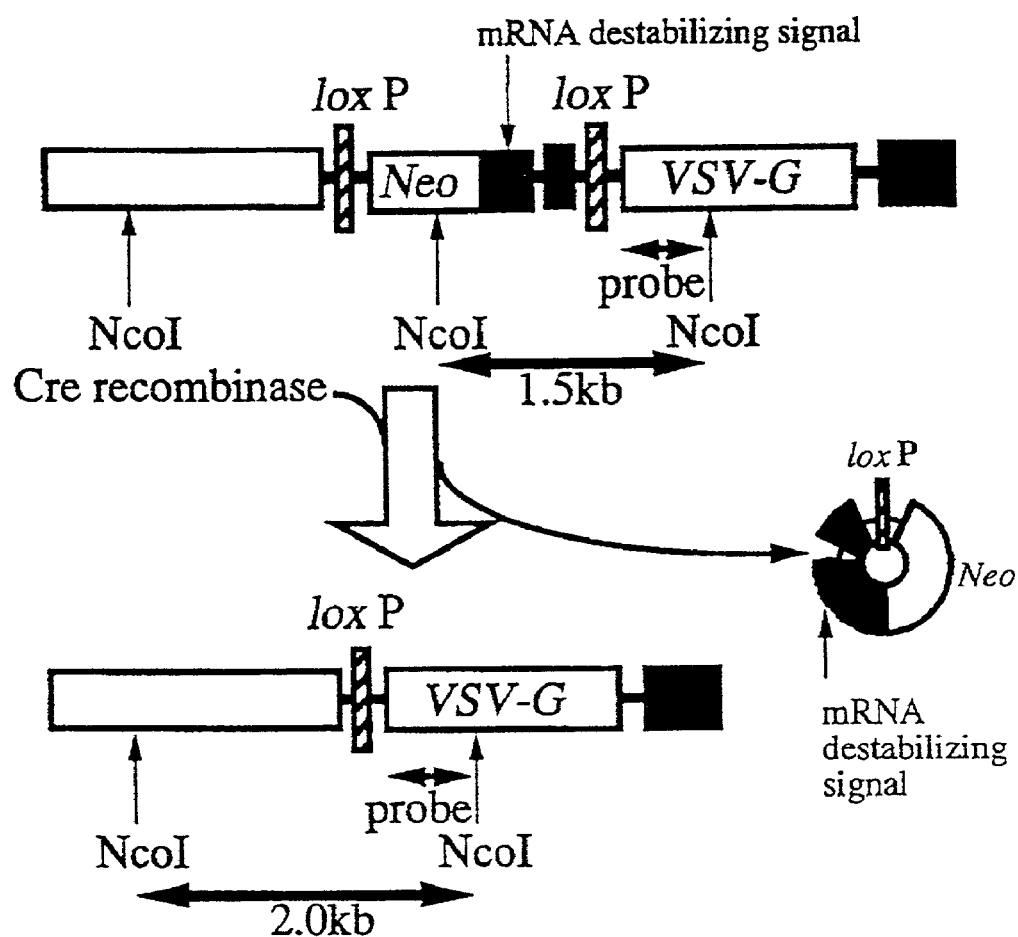
FIG. 10 shows an analysis on a change in chromosomes detected by the Southern blotting method before and after transferring the Cre recombinase.

By using PtG-L1 and PtG-S2 cells containing the MLV vector DNA encoding lacZ, protein samples were prepared under the introduction of the Cre recombinase (after transferring) and without transferring the Cre recombinase (i.e., corresponding to the state before transferring) similar to Example 2. Four days after the transfer of the Cre recombinase, the cells were solubilized with a DNA extract solution, digested with proteinase K and then extracted with phenol to thereby prepare genomic DNA. The genomic DNA was digested with NcoI, electrophoresed on an agarose gel and transferred onto a positively charged nylon membrane (Hybond N+, mfd. by Amesham) by capillary transfer. Detection was effected by using as a probe a $^{32}$P-labeled MluI-NcoI fragment (0.7 kb) in the VSV-G translated region as shown in FIG. 10. Consequently, the VSV-G expression units varied from 1.2 kb to 2.0 kb (PtG-L1) and from 1.5 kb to 2.0 kb (PtG-S2) by transferring the Cre recombinase as expected. Prior to the transfer of the Cre recombinase, PtG-L1 differed from PtG-S2 by 0.3 kb due to the absence of the short-lived mRNA sequence. After transferring the Cre recombinase, therefore, their structures became identical with each other. This fact well agreed with the assumption in FIG. 10. Thus, it was indicated that the neomycin resistance gene and the polyA addition signal located between the loxP sequences were efficiently cut off by the Cre recombinase from the prepackaging cells, thus causing a shift of the expression products as shown in Example 12. When the band densities were taken into consideration, PtG-S2 contained more VSV-G expression units than PtG-L1 did, which might be one of the factors causing the production of much VSV-G gene product by PtG-S2.

Example 14

Proof of the Absence of any Replication Competent Retrovirus (RCR) in Pseudotyped Retrovirus Produced by Prepackaging Cells In accordance with the conventional method ("Idenshi Chiryo no Kiso Gijutsu", Yodosha, 1996), M. dunni cells were infected with $5 \times 10^6$ i.u./ml of the pseudotyped retrovirus prepared from the PtG-S2 cells containing the MLV vector encoding lacZ at an m.o.i. of 5. After repeating the transfer of a 1/10 portion thereof thrice at intervals of four days, the liquid culture medium was taken up and added to PG-4 S+L-cells in the presence of DEAE-dextran. When the liquid culture medium from Mink 4070A cells containing the RCR was added to PG-4 S+L-cells at the same time, focuses were observed after four days. In contrast thereto, when the RCR which might be contained in the pseudotyped retrovirus prepared from the PtG-S2 cells was amplified by M. dunni, no focus was observed even after eight days similar to the uninfected one. These results indicated that $5 \times 10^6$ i.u./ml of the pseudotyped retrovirus prepared from the PtG-S2 cells was free from any RCR.

Example 15

Proof of the Absence of any Adenovirus in Pseudotyped Retrovirus Produced by Prepackaging Cells Although the method for transferring the Cre recombinase into prepackaging cells as described herein is not restricted to adenoviruses as described above, it is highly effective to use adenoviruses for achieving highly efficient and reproducible transfer. On the other hand, it is to be avoided from a clinical viewpoint that a pseudotyped retrovirus produced by prepackaging cells contain any adenovirus. Therefore, it was examined in the following manner whether or not a pseudotyped retrovirus contained any adenovirus.

The Cre recombinase was transferred into the PtG-S2 containing the MLV vector DNA encoding lacZ by using an adenovirus (AxCANCre) in the same manner as the one described in Example 2. The liquid culture medium was replaced by a fresh one everyday and the cells were carefully washed thrice with the liquid culture medium at every replacement to thereby eliminate the adenovirus which might remain therein. The adenovirus which might be contained in $5 \times 10^4$ i.u./ml of the pseudotyped retrovirus prepared from the sample of four days after the transfer (washing: nine times) was detected by using 293 cells in accordance with the conventional method ("Biomanual Series 4: Idenshi Donyu to Hatugen Kaisekiho", Yodosha, 1994). When infected with AxCANCre, more than 50% of the 293 cells were denatured during 12 days after the infection even under such conditions as allowing the presence of a single adenovirus. In contrast thereto, the 293 cells infected with $5 \times 10^4$ i.u./ml of the pseudotyped retrovirus showed no denaturation, which indicated that these cells were free from any adenovirus.

When the adenovirus was detected in the same manner with the use of 293 cells from an unwashed sample two days after the transfer of the Cre recombinase with the use of the adenovirus, the 293 cells underwent denaturation. However, this denaturation was weakened by simultaneously eliminating the adenovirus in the sample by using an anti-adenovirus antibody bonded to Protein G Sepharose (mfd. by Pharmacia). Although further optimization is needed for the complete elimination, it seems possible to eliminate the adenovirus by the treatment with an antibody.

Example 16

Confirmation of the Occurrence of not Interference but Reinfection of VSV-G Pseudotyped Retrovirus on Packaging Cells with the Expression of VSV-G Gene Product on the Surface Thereof (1)

It has been considered that the receptors employed in the gene transfer by the VSV-G pseudotyped virus vector are not proteins, different from the case of usual retroviruss, but anionic lipids which exist abundantly on the cell surface such as phosphatidylserine. Accordingly, the receptor on the packaging cell surface might not saturated by the VSV-G gene product, different from usual retroviruss, and thus the packaging cells might be infected again with the VSV-G pseudotyped virus vector thus produced. From this viewpoint, the following experiment was carried out.

PtG-S2 cells free from the MLV vector encoding lacZ were pipetted into five 24-well plates at a density of $3 \times 10^4$ cells/well. On the next day, the cells contained in the half of one plate were infected with AxCANCre at an m.o.i. of 10. The uninfected cells and the infected ones (during four days after the infection) were infected every day with 10 and 100 i.u./well of the VSV-G pseudotyped retrovirus encoding lacZ involving both of one having the Cre recombinase transferred thereinto and one having no Cre recombinase. Next, the cells were fixed and stained with X-gal by the above-mentioned methods. As a result, PtG-S2 having the Cre recombinase transferred thereinto and showing the expression of VSV-G were stained with X-gal in every plate at a level comparable or superior to that of the cells having no Cre recombinase and showing no expression of VSV-G. This result indicated that the VSV-G pseudotyped retrovirus encoding lacZ infected the packaging cells regardless of the presence of the VSV-G gene product on the packaging cells. Then the experiment as will be described in Example 17 was effected in the presence of a large amount of the VSV-G pseudotyped retrovirus.

Example 17

Confirmation of the Occurrence of not Interference but Autoinfection of VSV-G Pseudotyped Retrovirus on Packaging Cells with the Expression of VSV-G Gene Product on the Surface Thereof (2)

Into the PtG-S2 cells free from the MLV vector encoding lacZ in two plates was transferred the Cre recombinase (after transferring), while no Cre recombinase was transferred into the same PtG-S2 cells in other two plates (i.e., corresponding to the state before transferring) in the same manner as Example 2. Three days after the transfer of the Cre recombinase, the cells were transferred. On the next day, the cells were infected with the VSV pseudotyped virus vector containing the MLV vector encoding lacZ, which had been prepared separately, at an m.o.i. of 3. The transfer was carried out to prevent the cells from reaching confluence. It has been confirmed that this procedure largely affected the cells with the expression of VSV-G. Two days after the infection with the MLV vector encoding lacZ, the cells in one plate of each case were fixed and stained with X-gal in accordance with the methods as described above. The cells in another plate of each case were immunologically stained by the above-mentioned method to detect the VSV-G gene product. As a result, the lacZ gene had been transferred by the VSV-G pseudotyped virus vector into the PtG-S2 free from the MLV vector encoding lacZ, regardless of The transfer of the Cre recombinase, thus showing X-gal staining. The results of the immunological staining indicated that the VSV-G gene product was produced only in the cells into which the Cre recombinase had been transferred. These results pointed out that the VSV-G pseudotyped virus vector did not interfere but infected the producing cells per se, differing from usual retroviruss.

As mentioned above, it has been reported that VSV-G pseudotyped virus vector-producing cells can be prepared by regulating the expression of the VSV-G gene product with the use of tetracycline. In these reports, however, it has been pointed out that the expression of the VSV-G gene product cannot be perfectly regulated by tetracycline and thus $10^2$ to $10^4$ i.u./ml of the VSV-G pseudotyped virus vector capable of reinfecting the producing cells is continuously produced. The present results indicate that the VSV-G pseudotyped virus vector thus produced in a small amount during the maintenance of the packaging cells might reinfect the packaging cells per se. Consequently, there is a risk that the chromosomes in the packaging cells would remain continuously unstable due to the gene transfer by the VSV-G pseudotyped virus vector. As Example 10 shows, on the other hand, the prepackaging cells PtG-S2 produce no VSV-G pseudotyped virus vector before the treatment with the Cre recombinase. Thus, it is possible thereby to produce the VSV-G pseudotyped virus vector stably.

Example 18

Inhibition of Infection with VSV-G Pseudotyped Virus Vector by Heparin

As described above, it was indicated that the VSV-G pseudotyped virus vector would reinfect the packaging cells. Therefore it was anticipated that the recovery yield of the VSV-G pseudotyped virus vector could be elevated by inhibiting this reinfection. The reinfection might be prevented by circulating the liquid culture medium to thereby separate the VSV-G pseudotyped virus vector from the packaging cells and by specifying a substance capable of inhibiting the reinfection and adding it in the recovery step. Since it was found out that heparin which is a negatively charged, high-molecular weight substance inhibited the reinfection, its effect was examined by the following experiment.

Figure 11:
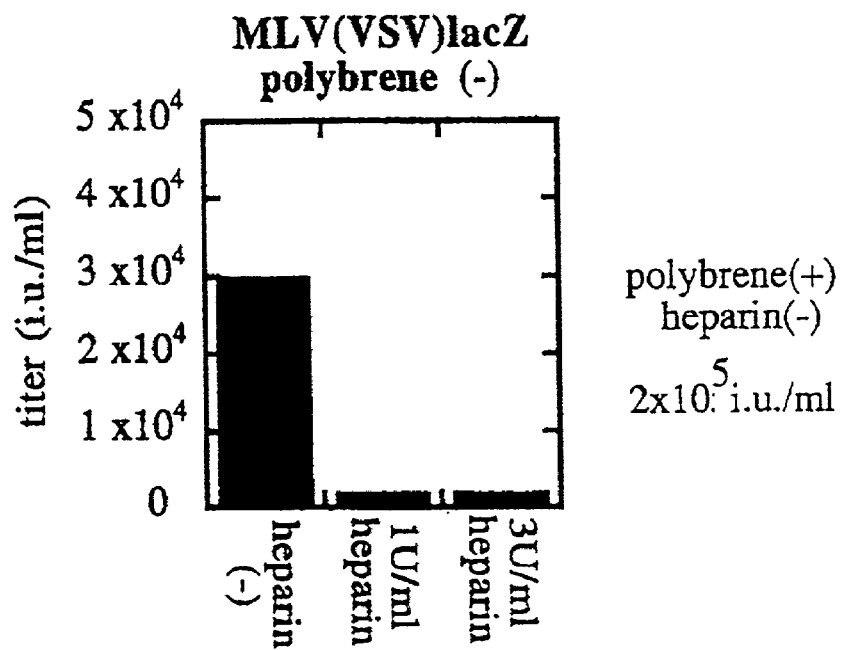
FIG. 11 shows an effect of heparin on the viral trnasduction.
Figure 11:
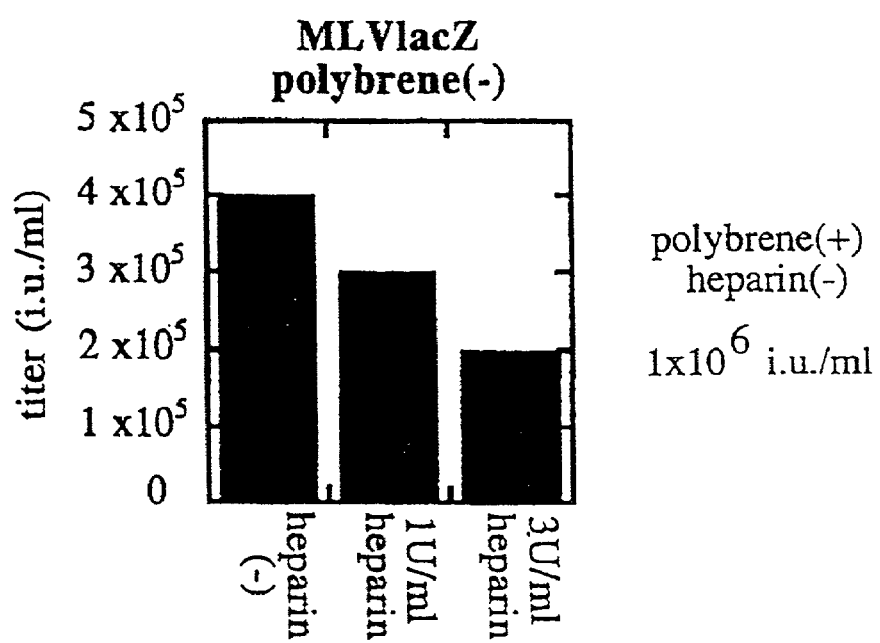

By using the above-mentioned method, measurement was made on the titers of the VSV-G pseudotyped virus vector encoding β-galactosidase (lacZ) and another retrovirus vector having an amphotropic MLV envelope in the presence of 0, 1 and 3 U/ml of heparin (mfd. by Novo Nordisk) without adding polybrene (8 μg/ml). FIG. 11 shows the results. Compared with the retrovirus vector having an amphotropic MLV envelope, the VSV-G pseudotyped virus vector showed a considerable decrease in its titer due to heparin. This is seemingly because heparin would have the effect of inhibiting the infection with the VSV-G pseudotyped virus vector.

Example 19

Increase in the Recovery Yield of VSV-G Pseudotyped Virus Vector by Heparin

As stated above, heparin exhibited the effect of inhibiting the infection with the VSV-G pseudotyped virus vector. Accordingly, it was examined whether or not the reinfection could be inhibited and the recovery yield could be thus increased by adding heparin in the step of the recovery of the VSV-G pseudotyped virus vector from the packaging cells.

The Cre recombinase was transferred into the PtG-S2 cells containing the MLV vector encoding lacZ in the same manner as Example 2. Two or four days after the transfer of the Cre recombinase, 1 U/ml or 3 U/ml of heparin was added to the liquid culture medium. Then the titer of the VSV-G pseudotyped virus vector thus produced was measured. As a result, it was found out that the addition of heparin resulted in an increase in the recovery yield by two to four times compared with the one achieved without adding heparin.

Because of the employment of an anticoagulant in the clinical field, heparin seemingly suffers from no problem in safety. When heparin was diluted, the infectivity of the VSV-G pseudotyped virus vector was restored. Namely, the actions thereof are reversible and thus heparin could be eliminated during the operation.

Example 20

Stability of Prepackaging Cells PtG-S2

The stability of PtG-S2 as prepackaging cells was examined.

The Cre recombinase was introduced into PtG-S2 cells containing the MLV vector DNA encoding lacZ cultured continuously for three months and the same PtG-S2 cells newly thawed from liquid nitrogen. Also preparation was made of the same PtG-S2 cells in which no Cre recombinase was transferred, similar to Example 16. When the titers of the VSV-G pseudotyped virus vector thus produced were examined by the above-mentioned method, no VSV-G pseudotyped virus vector was detected from the cells of both cases with no transfer of the Cre recombinase, while the cells having the Cre recombinase introduced thereinto in both cases were comparable to each other in the VSV-G pseudotyped virus vector productivity. These facts indicated that PtG-S2 had a high stability as prepackaging cells.

Example 21

Concentration of VSV-G Pseudotyped Virus Vector by Ultracentrifugation

By using an ultracentrifuge (Beckman L-60E), the VSV-G pseudotyped virus vector was concentrated.

$2.2 \times 10^8$ i.u./480 ml of the VSV-G pseudotyped virus vector was pipetted in 40 ml portions into 12 sterilized ultracentrifugal tubes (Beckman No. 344058) and concentrated by centrifuging at 19,500 rpm with the use of an SW28 rotor for one hour and 40 minutes twice, i.e., six tubes each time. After the completion of the concentration, the supernatant in each tube was eliminated and 0.2 ml of FCS-free DMEM was added to the residue. After allowing the tube to stand on ice for one hour, the contents were suspended by occasionally shaking the tubes gently. Then the tube was allowed to stand on ice for additional one hour. Thus, 1.5 ml of $4 \times 10^7$ i.u./ml of the VSV-G pseudotyped virus vector was obtained (recovery yield: 69%). Further, the thus concentrated VSV-G pseudotyped virus vector was introduced into an ultracentrifugal tube (Beckman 358650) and concentrated by ultracentrifuging with the use of an SW41 rotor at 19,500 rpm for one hour and 40 minutes. The supernatant was eliminated with a syringe and 0.05 ml of FCS-free DMEM was added to the residue followed by suspending on ice. Thus 0.08 ml of the VSV-G pseudotyped virus vector concentrated to $1 \times 10^9$/ml was obtained. In the second run of ultracentrifugation, a recovery yield of 53% was established. Namely, 37% of the starting VSV-G pseudotyped virus vector had been thus concentrated to $1 \times 10^9$/ml.

Example 22

Sustenance of the Expression of Gene Transferred by VSV-G Pseudotyped Virus Vector Human fibroblasts FLY and rat fibroblasts 3Y1 were infected with the following retrovirus vectors, each carrying lac Z (β-galactosidase) having a nuclear transport signal in the vector RNA, at an m.o.i. of 1 and the sustenance of the expression of lacZ was studied.

1. Concentrated VSV-G pseudotyped virus vector.
2. Unconcentrated VSV-G pseudotyped virus vector.
3. A retrovirus vector having an amphotropic envelop.

After the transduction, the cells were newly passaged at intervals of three days and lacZ located in the nuclei in some of these cells was examined by X-gal staining. Until the 13th day after the infection, no difference in the sustenance of the expression of lacZ was observed among these three retrovirus vectors. It was therefore considered that the VSV-G pseudotyped virus vector would ensure the stable expression of the transferred gene similar to the retrovirus vector having an amphotropic envelope.

Example 23

Construction of pBabe loxpuro-d Containing Short-Lived mRNA Sequence in Resistance Gene The NcoI-site located between the puromycin resistance gene and the polyA addition signal in pBabe loxpuro prepared by the above-mentioned method was cleaved with this restriction enzyme and blunt-ended with a Klenow fragment. Then the short-lived mRNA sequence of chicken c-fos (AU rich element: ARE) of 414 bps as described above and blunt-ended with a Klenow fragment was inserted thereinto to give pBabe loxpuro-d.

Example 24

Construction of VSV-G Pseudotyped Retrovirus Vector Capable of Initiating the Gene Expression of Full-Length Vector RNA by Cre Recombinase pBabe loxpurolacZ wherein lacZ had been inserted into the multicloning site of pBabe loxpuro was transferred into PtG-S2 via lipofection. Then the cells into which the insert had been transferred were screened by using the resistance against puromycin. The thus screened cells were not cloned but proliferated. Into these cells was transferred the Cre recombinase with AxCANCre and the titer of the VSV-G pseudotyped retrovirus vector thus produced was measured by using lacZ as an indication. The cells in which Cre recombinase was introduced thereinto began to produce the VSV-G pseudotyped retrovirus vector and showed a productivity thereof of $2 \times 10^4$ i.u./ml five to eight days after the transfer. When lacZ was stained with X-gal, some of the cells with the transfer were stained eight days after the transfer, while no expression of lacZ was observed in the cells into which no Cre recombinase had been transferred. These facts indicated that the gene encoded by the vector RNA could produce the VSV-G pseudotyped retrovirus vector under the strict regulation of the expression of the Cre recombinase. Thus, it has become possible to produce a large amount of a retrovirus vector having a vector RNA encoding a gene which exerted considerable effects (e.g., cytotoxicity) stably.

Example 25

Proof of the Absence of any Replication Competent Retrovirus (RCR) in Pseudotyped Retrovirus Produced by Prepackaging Cells (2)

The procedures described in Example 14 were improved and thus the following results were obtained. In accordance with the conventional method ("Idenshi Chiryo no Kiso Gijutsu", Yodosha, 1996), *M. dunni* cells were infected with $1 \times 10^7$ i.u./ml of the pseudotyped retrovirus prepared from the PtG-S2 cells containing the MLV vector encoding lacZ at an m.o.i. of 5. After repeating the transfer of a 1/10 portion thereof thrice at intervals of four days, the liquid culture medium was taken up and added to PG-4 S+L-cells in the presence of DEAE-dextran. When the liquid culture medium from Mink 4070A cells containing the RCR was added to PG-4 S+L-cells at the same time, focuses were observed after four days. In contrast thereto, when the RCR which might be contained in the pseudotyped retrovirus prepared from the PtG-S2 cells was amplified by *M. dunni*, no focus was observed even after eight days similar to the uninfected one. These results indicated that $1 \times 10^7$ i.u./ml of the pseudotyped retrovirus prepared from the PtG-S2 cells was free from any RCR.

Example 26

Proof of the Absence of any Adenovirus in Pseudotyped Retrovirus Produced by Prepackaging Cells (2)

The procedures described in Example 15 were improved and thus the following results were obtained. The Cre recombinase was introduced into the PtG-S2 containing the MLV vector DNA encoding lacZ by using an adenovirus (AxCANCre) in the same manner as the one described in Example 2. The liquid culture medium was replaced by a fresh one everyday and the cells were carefully washed with the liquid culture medium at every replacement. The liquid culture medium employed in washing was completely removed by pipetting to thereby eliminate the adenovirus which might remain therein. Three to five days after the transfer (washing: at least six times), the adenovirus which might be contained in $2 \times 10^6$ i.u./ml of the pseudotyped retrovirus prepared from the sample was detected by using 293 cells in accordance with the conventional method ("Biomanual Series 4: Idenshi Donyu to Hatsugen Kaisekiho", Yodosha, 1994). When infected with AxCANCre, more than 50% of the 293 cells were denatured for 12 days after the infection even under such conditions as allowing the presence of a single adenovirus-infected unit. In contrast thereto, the 293 cells infected with $2 \times 10^6$ i.u./ml of the pseudotyped retrovirus showed no denaturation, which indicated that these cells were free from any adenovirus.

A liquid culture medium containing $1 \times 10^6$ i.u./ml of this adenovirus vector was treated with a rabbit polyclonal antiadenovirus antibody (assigned by Dr. Shiraki, Department of Virology, The Institute of Medical Science, The University of Tokyo) bonded to Protein G Sepharose (mfd. by Pharmacia) for one hour at 4° C. Then the supernatant was taken up and an attempt was made to detect the adenovirus by using 293 cells similar to the above case. The 293 cells showed no denaturation within 12 days following the infection, which indicated that the adenovirus vector contained in the liquid culture medium had been completely eliminated by this antibody.

We claim:

1. An expression vector comprising a promoter, a recombinase recognition sequence, a selectable drug-resistance gene having an mRNA-destabilizing sequence, a polyA addition signal, a recombinase recognition sequence, a gene encoding a viral structural protein, and a polyA addition signal, arranged in this order, which produces a short-lived transcript of the drug-resistance gene and wherein said promoter transcribes the gene encoding a viral structural protein in a prepackaging cell.

2. The expression vector as set forth in claim 1, in which the mRNA-destabilizing sequence is an mRNA-destabilizing sequence of a c-fos gene.

3. The expression vector as set forth in claim 1, in which the drug-resistance gene is selected from the group consisting of a neomycin resistance gene, a puromycin resistance gene and a hygromycin resistance gene.

4. Cells into which the expression vector as set forth in claim 1 has been transferred and selected with the drug.

5. A process for producing cells expressing a gene encoding a viral structural protein in the expression vector as set forth in claim 1, comprising:
   (a) transferring the expression vector into cells,
   (b) selecting cells which express the drug-resistance gene from the transferred expression vector, and
   (c) expressing the gene encoding a viral structural protein in the expression vector in the selected cells.

6. A process for expressing a gene encoding a viral structural protein in the expression vector as set forth in claim 1, comprising:
   (a) transferring the expression vector into cells having gag and pol genes of a retrovirus,
   (b) selecting prepackaging cells which express the drug-resistance gene from the transferred expression vector, and
   (c) expressing the gene encoding a viral structural protein in the expression vector in the selected prepackaging cells.

7. An expression vector comprising a promoter, a recombinase recognition sequence, a selectable drug-resistance gene having an mRNA-destabilizing sequence, a polyA addition signal, a recombinase recognition sequence, a foreign gene, and a polyA addition signal, arranged in this order, which produces a short-lived transcript of the drug-resistance gene and wherein said promoter transcribes the foreign gene in a prepackaging cell.

8. The expression vector as set forth in claim 7, in which the mRNA-destabilizing sequence is an mRNA-destabilizing sequence of a c-fos gene.

9. The expression vector as set forth in claim 7, in which the drug-resistance gene is selected from the group consisting of a neomycin resistance gene, a puromycin resistance gene and a hygromycin resistance gene.

10. Cells into which the expression vector as set forth in claim 7 has been transferred and selected with the drug.

11. A process for producing cells expressing a foreign gene in the expression vector as set forth in claim 7, comprising:
    (a) transferring the expression vector into cells,
    (b) selecting cells which express the drug-resistance gene from the transferred expression vector, and
    (c) expressing the foreign gene in the expression vector in the selected cells.

12. A process for expressing a foreign gene in the expression vector as set forth in claim 7, comprising:
    (a) transferring the expression vector into cells having gag and pol genes of a retrovirus,
    (b) selecting prepackaging cells which express the drug-resistance gene from the transferred expression vector, and
    (c) expressing the foreign gene in the expression vector in the selected prepackaging cells.

13. An expression vector to be expressed in a prepackaging cell comprising a first LTR of a retrovirus genome and a packaging signal, a recombinase recognition sequence, a selectable drug-resistance gene having an mRNA-destabilizing sequence, a polyA addition signal, a recombinase recognition sequence, a foreign gene, and a second LTR of a retrovirus genome, arranged in this order, which produces a short-lived transcript of the drug-resistance gene.

14. The expression vector as set forth in claim 13, in which the mRNA-destabilizing sequence is an mRNA-destabilizing sequence of a c-fos gene.

15. The expression vector as set forth in claim 13, in which the drug-resistance gene is selected from the group consisting of a neomycin resistance gene, a puromycin resistance gene and a hygromycin resistance gene.

16. Cells into which the expression vector as set forth in claim 13 has been transferred and selected with the drug.

17. A process for producing cells expressing a foreign gene in the expression vector as set forth in claim 13, comprising:
    (a) transferring the expression vector into cells,
    (b) selecting cells which express the drug-resistance gene from the transferred expression vector, and (c) expressing the foreign gene in the expression vector in the selected cells.

18. A process for expressing a foreign gene in the expression vector as set forth in claim 13, comprising:
(a) transferring the expression vector into cells having gag and pol genes of a retrovirus,
(b) selecting prepackaging cells which express the drug-resistance gene from the transferred expression vector, and
(c) expressing the foreign gene in the expression vector in the selected prepackaging cells.

\* \* \* \* \*

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
-continued

<400> SEQUENCE: 1
tcgacgcaga tctcacgtga tttaaatat                                              29

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgatatttaa atcacgtgag atctgcg                                                27
```